United States Patent [19]
Dennis et al.

[11] Patent Number: 5,981,483
[45] Date of Patent: Nov. 9, 1999

[54] COMPOSITIONS COMPRISING MODULATORS OF CYTOKINES OF THE TGF-β SUPERFAMILY

[75] Inventors: James W. Dennis, Etobicoke; Michael Demetriou, Toronto, both of Canada

[73] Assignee: Mount Sinai Hospital Corporation, Toronto, Canada

[21] Appl. No.: 08/737,045

[22] PCT Filed: May 4, 1995

[86] PCT No.: PCT/CA95/00290

§ 371 Date: Mar. 20, 1997

§ 102(e) Date: Mar. 20, 1997

[87] PCT Pub. No.: WO95/30900

PCT Pub. Date: Nov. 16, 1995

Related U.S. Application Data

[63] Continuation of application No. 08/237,715, May 4, 1994, abandoned.

[51] Int. Cl.$^6$ ............................ C07K 14/47; A61K 38/04
[52] U.S. Cl. .................................... 514/12; 514/2; 514/8; 514/885; 530/350
[58] Field of Search ............................ 514/2, 8, 12, 885; 530/350

[56] References Cited

FOREIGN PATENT DOCUMENTS

| 2002011 | 5/1990 | Canada . |
|---|---|---|
| PCT/US91/ 04449 | 12/1991 | WIPO . |
| PCT/US92/ 03825 | 11/1992 | WIPO . |

OTHER PUBLICATIONS

Massague, J., 1990, Annu. Review Cell Biol. 6:597–641.
Ewen, M. E. et al., Cell 74, 1009–1020, 1993.
Koff, A. et al., Science 260, 536–539, 1993.
Silberstein, G. and Daniel, W.D., Science 237:291–293, 1987.
Russell, W.E. et al., 1988, Proc. Natl. Acad. Sci. USA 85:5126–5130.
Roberts, A.B. et al., Proc. Natl. Acad. Sci. USA, 78(9):5339–5343, 1981.
Roberts, A.B. et al., Nature 295:417–419, 1982.
Twardzik, D.R. and Sherwin, S.A., J. Cell. Biochem. 28:289–297, 1985.
Tucker, R.F. et al., Science 226:705–707, 1984.
Sporn, M.B. et al., Science 219:1329–1331, 1983.
Roberts, A.B. et al., Proc. Natl. Acad. Sci. USA 83:4167–4171, 1986.
Mustoe, T.A. et al., Science 237:1333–1336, 1987.
Kehrl, J.h. et al., J. Immunol. 137:3855–3860, 1986.
Kehrl, J.H. et al., 1986, J. Exp. Med. 163:1037–1050.
Ristow, H.J., 1986, PNAS, USA 83:5531–5533.
Lotz, M. and Seth, P., Annals New York Academy of Sciences 685:501–511, 1993.
Baecher–Allan, C.M. and Barth, R.K., Regional Immunology 5(3–4):207–217, 1993.
Burt, A.D., J. of Pathology 170:105–114, 1993.
Anscher, M.S. et al., N. Engl. J. Med. 328(22):1592–1598, 1993.
Border, W.A. et al., Nature 360:361–364, 1992.
Martin, M., et al., Radiation Research 134:63–70, 1993.
Connor, B. et al., J. Clin Invest. 83:1661–1666, 1989.
Kulozik, M. et al., J. Clin. Invest. 86:917–922, 1990.
Rosen, V. and Thies, R.S., Trends in Genetics, 8(3):97–102, 1992.
Padgett, R.V. et al., 1987, Nature, 325:81–84.
Mason, A.J. et al., 1985, Nature 318:659–663.
Ling, N. et al., Nature 321:779–782, 1986.
Cate, R.L. et al., Cell 45:685–698, 1986.
Massague, J., Cell, 69:1067–1070, 1992.
Lin, H. Y. et al., Cell 68:775–785, 1992.
Schultz–Cherry, S. and Murphy–Ullrich, J.E., J. Cell Biol. 122(4), 923–932, 1993.
Massague, J., Curr. Biol. 1(2), 117–119, 1991.
Yamaguchi, Y. et al., Nature 346:281–284, 1990.
Kellermann, J. et al., J. Biol. Chem. 264(24):14121–14128, 1989.
Puck, T.T. et al., Proc. Natl. Acad. Sco. USA 59, 192–199, 1968.
Daveau, M. et al., FEBS Lett. 273(1,2), 79–81, 1990.
Dickson, I.R., Poole, A.R., Veis, A., Nature 256, 430–432, 1975.
Triffitt, J.T., Gebauer, U., Ashton, B.A., Owen, M.E., Nature 262, 226–227, 1976.
Rauth, G. et al., Eur. J. Biochem. 204, 523–529, 1992.
Colclasure, G.C. et al., J. Clin. Endocrin. Metabolism 66(1), 187–192, 1988.
Cayatte, A.J., Kumbla, L., Subbiah, M.T.R., J. Biol. Chem. 265(10), 5883–5888, 1990.
Basler, K. et al. Cell, 73:687–702, 1993.
Frolik, C.A. et al., 1983, Proc. Natl. Acad. Sci. USA 80:3676–3680.

(List continued on next page.)

*Primary Examiner*—Prema Mertz
*Attorney, Agent, or Firm*—Merchant, Gould, Smith, Edell, Welter & Schmidt

[57] ABSTRACT

Compositions consisting of at least one TGFb receptor II homo 1b (TRH1b) subdomain or at least one TGFb receptor II homology 1 (TRH1) domain and a carrier, auxiliary or excipient. The TRH1b subdomain has a sequence with the following amino acid pattern:
Cys—$X_j$—Lys/Arg—$X_k$—Ser/Thr—$X_l$—Cys—$X_m$—Asp—$X_n$—Asp/Glu, wherein $X_j$, $X_k$, $X_l$, $X_m$, $X_n$, represent any amino acid and j is 4 to 5, k is 2 to 6, l is 4 to 9, m is 0 to 2, and n is 5 to 6. The TRH1 domain has a sequence with the following amino acid pattern:
Cys—$X_h$—Asn/Gln—$X_i$—Cys—$X_j$—Lys/Arg—$X_k$—Ser/Thr—$X_l$—Cys—$X_m$—Asp—$X_n$—Asp/Glu, wherein $X_h$, $X_i$, $X_j$, $X_k$, $X_l$, $X_m$, $X_n$, represent any amino acid and h is 8 to 14, i is 12 to 16, j is 4 to 5, k is 2 to 6, l is 4 to 9, m is 0 to 2, and n is 5 to 6.

7 Claims, 18 Drawing Sheets

OTHER PUBLICATIONS

Roberts, A.B. et al., 1983, Biochemistry 22:5692–5698.
Childs, C.B. et al., 1982, Proc. Natl. Acad. Sci. USA 79:5312–5316.
Kellerman, J. et al., Biochem. J. 247:15–21, 1987.
Farmer, P.S., in Drug Design, EJ Ariens, Ed. (Academic Press, New York, 1980) vol. 10, pp. 119–143.
Ball, J.B. and Alewood, P.F., J. Mol. Recognition 3:55, 1990.
Morgan, B.A. and Gainer, J.A., Annu. Rep. Med. Chem. 24, Chptr, 26, 243–252, 1989.
Friedlinger R.M., Trends Pharmacol. Sci. 10, 270–274, 1989.
Merrifield, R.B., 1963, J. Am. Chem. Assoc. 85:2149–2154.
Wozney, J.M., et al., Science 242, 1528–1534, 1988.
Mercken, L. et al., Nature 316, 647–651, (1985.
Ebner, R. et al., Science 260, 1344–1348, 1993.
Attisano, L. et al., Cell 75, 671–680, 1993.
Franzen, P. et al., Cell 75, 681–692, 1993.
Bassing, C. H., et al., Science 263, 87–89, 1994.
Wrana, J.L., et al., Cell 71, 1003–1014, 1992.
McDonald, N.Q. and Hendrickson, W.A., Cell 73:421–424, 1993.
Demura, R. et al., Biochem. Biophys. Res. Com. 185(3): 1148–1154, 1992.
Ashton, B.A. and Smith, R., Clinical Science 58:435–438, 1980.
Colletta, G. et al., Cancer Research 49:3457–3462.
Lebreton, J.P. and Joisel, F., Clin. Invest. 64:1118–1129, 1979.
O'Connor–McCourt, M.D. and Wakefield, L.M., The J. Biol. Chem. 262(29): 14090–14099, 1987.
Dziegielewska, K. et al. "The Complete cDNA and Amino Acid Sequence of Bovine Fetuin", The Journal of Biological Chemistry, vol. 265; 8:4354–4357, 1990.
Begbie et al (1974) Biochimica et Biophysica Acta, 371, pp. 549–576.
Smith et al. (1987) Science, vol, 238: 1704–1707.
Bowie et al. Science vol. 247, pp. 1306–1310, 1990.

FIGURE 6

Multiple alignment project: FETUIN    17-NOV-93    09:31:39

```
bov  IKSFVLLFCLAQLWGCSIPLDPVAGYKEPACDDPDIEQAALAAVDYINKHLPRGYKHILNQIDSVKVHPRRPIGEVYDI  80
pig     ILFFCLAQLWGCRAVPHGPILGYREPACDDVETEQAALAAVDYINKHLPRGYKHTLNQVDSVKVIIPRRPAGEVEDI  76
shp  IKSFLLLFCLAQLCSCRSIPLDPIAGYKEPACDDPDTEQAALAAVDYINKHLPRGYKHTLNQIDSVKVIIPRRPTGEVYDI 80
rat  IKSLVLLLCFAQLWSCQSAPQGAGLGFRELACDDPETEHVALIAVDYLNKHLLQGFRQILNQIDXVKVLSRRPFGEVYEL 80
hum  --------------APHGPGLIYRQPYCDDPETEEAALVAIDYINQNLPLGYKHTLNQIDEVKVHPQOPSGELESI  62
```

TRH1a        TRH1b

```
bov  EIDTLETTCHVLDPTPLANCSVRQQIQHAVEGDCDLHVLKQDGQFSVLFUKCDSSPDSAEDVRKLCPDCPLLAPLNDSRV 160
pig  EIDTLETTCHVLDPTPLANCSVRQITEHAVEGDCDFHVLKQDGQFSVLFAKCDSSPDSAEDVKCPACPLLAPLNDSRV 156
shp  EIDTLETTCHVLDPTPLVNCSVRQQTEHAVEGDCDIHVLKQDGQFSVLFUKCDSSPDSAEDVRKLCPDCPLLAPLNXSQV 160
rat  EIDTLETTCHALDPTPLANCSVRQQAEHAVEGDCDFHILKQDGQFRVLAQCSTPDSAEDVRKFCPECPILIRFNDIKV 160
hum  EIDTLETTCHVLDPTPVARCSVRQTKEHAVEGDCDFQLLKLDGKFSVVYAKCDSSPDSAEDVRKNCTDCPLLAPLNDIRV 142
```

```
bov  VHAVEVALAIIFNAESNGSYLQLVEISRAQFVPLPVSVSVEFAVAATDCIAKEVNDPTKCNLLAEKQYGFCKGSVIQKALG 240
pig  VHAAESALAAFNAQSNGSYLQLVEISRAQIVPLSASVSVEFAVAMTDCVAKEAYSPTKCNLLVEKQYGFCKGTVTAK-VN 235
shp  VHAAEVALATFNAQNNGSYFQLVEISRAQFVPLPCSVSVEFAVAATDCIAKEVUDPTKCNLLAEKQYGFCKGSVIQKALG 240
rat  VHIVKTALAAFNAQHNGTYFKLVEISRAQXVPFPVSFLVEFVIAATDCTGOEVTDPRKCNLLAEKQYGFCKATILHR-LG 239
hum  VHAAAALAAFNAQHNGSXFQLEEISRAQLVPLPPSIYVEFITVSGTDCYAKEAIEAAKCNLLAEKQYGFCKAILSEN-LG 221
```

```
bov  GEDVRVTCILFQTQPVIPQPQPDGAELAEAPSAVPDAACPTIPSAAGPPVASVVIGPSVVAVPL------PLHRAHYDLRHI 314
pig  GEDVAVTCTVFQTQPVVLQPQPAGADAGATPVVDAAATISII-LADYPAASLVVGPVVAVPP---GIFPVIRSHYDLRHS 311
shp  GEDVTVTCTLFQTQPVIPQPQPEGAEAGAPSAVPDAAVPD-AAVPAPSAAGLPVGSVVAGRSVVAVPLPLIRAHYDLRHI 319
rat  GEEVSVACKLFQTQPQPANANPAGPAPTYGOAAPVAPPAGPPESVVVGPVAVPLE------LPQIRTIEDLRHA 307
hum  GAEVAVTCTYFQTQPVTSOPQPEGANEAVPTPVVDPDAPPSPPLGAPGLPPAGSPPDSHVLEAAPPGHOLIRAHYDLRHI 301
```

```
bov  FSGVASVESSSGEAFHVGKTPIVGQPSIP----GGPV-RLCPGRIRYFKI  359
pig  FSGVASVESASGEAFHVGKTPXGAQPSIPAADGSYPVVRPCPGRIRIFKI  361
shp  FSGVASVESASGEAFHVGKTPIVGQPSVP-----GGPVILCPGRIRYFKI  364
rat  FSPVASVESASGEVLHSPK---VGQPGDACAA--GPVAPLCPGRVRYFKI  352
hum  FMGVVSLCSPSGEVSHPRKTRTVVQPSVGAAA--GPVVPPCPGRIRIFKV  349
```

FIGURE 8

```
                              TRH1
mTGF-betaRI       CGNED--HCEGQCCFSSLSIYDGFHVYQK-----------------GCFQ   72
hTGF-betaRII      CDNQK--SCMS-NC-SITSICEKPQEVC-VAVWRKNDEN-IT-LEIVCHD  103
bTHYROGLOBULIN    CSADYSGLLAFIVFLLDELT-A-RGFCCIQV--KTAGTPVS-I-PVCDD 1349
bFETUIN           CHVLDPTP-LA-NCSVRQQTQHAVEGDCDIHVL-KQDGQ-FSVLFTKC-D  133
                         a                          b
```

FIGURE 11

```
TRANSLATE of: m85079.gb_pr check: 1576 from: 336 to: 2036
generated symbols 1 to: 567.

LOCUS        HUMTGFBIIR    2090 bp    mRNA              PRI       14-JAN-1995
DEFINITION   Human TGF-beta type II receptor mRNA, complete cds.
ACCESSION    M85079
KEYWORDS     transforming growth factor-beta type II receptor.
SOURCE       Homo sapiens (tissue library: lambda zapII) cDNA to mRNA.
  ORGANISM   Homo sapiens . . .

M85079.pep  Length: 567  June 22, 1995 14:50  Type: P  Check: 5743   ..

1  MGRGLLRGLW  PLHIVLWTRI  ASTIPPHVQK  SVNNDMIVTD  NNGAVKFPQL

51  CKFCDVRFST  CDNQKSCMSN  CSITSICEKP  QEVCVAVWRK  NDENITLETV

101  CHDPKLPYHD  FILEDAASPK  CIMKEKKKPG  ETFFMCSCSS  DECNDNIIFS

151  EEYNTSNPDL  LLVIFQVTGI  SLLPPLGVAI  SVIIIFYCYR  VNRQQKLSST

201  WETGKTRKLM  EFSEHCAIIL  EDDRSDISST  CANNINHNTE  LLPIELDTLV

251  GKGRFAEVYK  AKLKQNTSEQ  FETVAVKIFP  YEEYASWKTE  KDIFSDINLK

301  HENILQFLTA  EERKTELGKQ  YWLITAFHAK  GNLQEYLTRH  VISWEDLRKL

351  GSSLARGIAH  LHSDHTPCGR  PKMPIVHRDL  KSSNILVKND  LTCCLCDFGL

401  SLRLDPTLSV  DDLANSGQVG  TARYMAPEVL  ESRMNLENAE  SFKQTDVYSM

451  ALVLWEMTSR  CNAVGEVKDY  EPPFGSKVRE  HPCVESMKDN  VLRDRGRPEI

501  PSFWLNHQGI  QMVCETLTEC  WDHDPEARLT  AQCVAERFSE  LEHLDRLSGR

551  SCSEEKIPED  GSLNTTK
```

COMPOSITIONS COMPRISING MODULATORS OF CYTOKINES OF THE TGF-β SUPERFAMILY

CROSS REFERENCE TO RELATED APPLICATIONS

This is a 371 of PCT application PCT/CA95/00290, filed May 4, 1995, which is a continuation of U.S. Ser. No. 08/237,715, filed May 4, 1994, now abandoned.

FIELD OF THE INVENTION

The present invention relates to methods and compositions for treating conditions requiring modulation of cytokines of the TGF-β superfamily, and methods for screening for compounds useful in treating such conditions.

BACKGROUND OF THE INVENTION

The transforming growth factor beta (TGF-β) superfamily is a group of cytokines that regulate many aspects of cellular function. The structural prototype for the gene superfamily is TGF-β. TGF-β is produced as a precursor and the precursor structure is shared by most of the members of the TGF-β superfamily. The superfamily includes the TGF-β family, the inhibin family, the DPP/VGl family and the Mullerian Inhibiting Substance Family.

The TGF-β family includes five members, termed TGF-β1 through TGF-β5, all of which form homodimers of about 25 kd (reviewed in Massague, Annu. Review Cell Biol. 6:597, 1990). The family also includes TGF-β1.2 which is a heterodimer containing a β1 and a β2 subunit linked by disulfide bonds. The five TGF-β genes are highly conserved over great evolutionary distances. The mature processed cytokines produced from the members of the gene family show almost 100% amino acid identity between species, and the five peptides as a group show about 60–80% identity.

All forms of TGF-β have been found to reversibly inhibit growth activity in normal, epithelial, endothelial, fibroblast, neuronal, lymphoid, and hematopoietic cell types (For review see Massague, 1990, Annu. Review Cell Biol. 6:597). In tissue culture, TGF-β has been shown to inhibit cell growth by blocking both cdk-4/cyclinD activation and cdk2/cyclinE activity, events required for G1 to S phase transition (M. E. Ewen, H. K. Sluss, L. L. Whitehouse, D. M. Livingston, Cell 74, 1009 (1993) and A. Koff, M. Ohtsuki, K. Polyak, J. M. Roberts, J. Massague, Science 260, 536 (1993)). The antiproliferative action of TGF-β has also been demonstrated in vivo (Silberstein and Daniel, 1987, Science 237:291–93; and Russell et al, 1988, Proc. Natl. Acad. Sci. U.S.A. 85:5126–30).

TGF-β can also stimulate cell proliferation although the effect may be secondary to other cellular responses. For example, TGF-β1 has been shown to promote the anchorage independent growth of normal rat kidney fibroblasts (Roberts et al., PNAS U.S.A. 78:5339, 1981; Roberts et al, Nature 295:417, 1982 and Twardzik et al., 1985, J. Cell. Biochem. 28:289, 1985) and it induces colony formation of AKR-2B fibroblasts (Tucker et al. Science 226:705, 1984). The inhibitory/stimulatory actions of TGF-β may depend on the cell type and the physiological state of the cells.

TGF-β is involved in mediation of cell adhesion. TGF-β action on normal mesenchymal, epithelial and lymphoid cells, and some tumor cell lines generally results in the up-regulation of cell adhesion. This up-regulation is mediated by enhanced synthesis and deposition of extracellular matrix components, decreased pericellular proteolysis, and modification of cell adhesion receptors (Massague, 1990).

Cellular differentiation processes of many cell lineages can be positively or negatively effected by TGF-β. TGF-β has been shown to exert positive effects on chondrocyte and osteogenic cell types (Massague, 1990).

The biological actions of TGF-β described above suggest a broad role for TGF-β in the physiologic setting. The ability of TGF-β to modulate DNA replication, cell differentiation, cell adhesion and extracellular matrix layout indicate a role for TGF-β in the generation and modification of signals that guide morphogenic events of embryogenesis. The activity of TGF-β as a promoter of extracellular matrix formation and a regulator of cell migration and development, is a major influence in inflammation and tissue repair processes. In fact, the administration of TGF-β1 into wound chambers or to incisional wounds has been shown to accelerate the wound healing response in general (Sporn et al., 1983, Science, 219:1329–31; Roberts et al., 1986, Proc. Natl. Acad. Sci. U.S.A. 83:4167–71; and Mustoe et al., 1987, Science 237:1333–36).

The TGF-β family of cytokines display an immunosuppressive activity in vitro and in vivo which is in part attributed to the antiproliferative action of TGF-β on lymphocytes (Kehrl et al 1986, J. Immunol. 137:3855), T-lymphocytes (Kehrl et al 1986, J. Exp. Med. 163:1037) and thymocytes (Ristow 1986, PNAS U.S.A. 83:5531). An excess of TGF-β activity in tissues may lead to an unbalanced deposition of extracellular matrix which may contribute to fibrosis, while a lack of TGF-β growth inhibitory activity may lead to oncogenic transformation.

Dis-regulation of TGF-β action has been implicated in the pathological processes of many diseases. TGF-β has been reported to be a pathogenic mediator in HIV infections and its associated diseases (Lotz, M. and Seth, P. Annals of the N.Y. Acad. of Sciences 685:501, 1993).

TGF-β has also been implicated in the development of fibrosis including pulmonary fibrosis (Baecher-Allan and Barth, Regional Immunology 5(3–4):207, 1993), and fibrosis associated with chronic liver disease (Burt, A. D., J. of Pathology 170:105, 1993), hepatic veno-occlusive and idiopathic interstitial pneumonitis, which are major causes of morbidity and mortality after bone marrow transplantation (Anscher M. S. et al. N.Engl.J.Med. 328:1592, 1993), kidney disease (Border et al., Nature 369:360:361, 1992), and radiotherapy or radiation accidents (Martin M. et al Radiation Research 134:63, 1993). TGF-β2 has been found to be elevated in the eye of humans with proliferative vitreoretinopathy and in the skin in systemic sclerosis (Connor et al. J. Clin Invest. 83.:1661, 1989 and Kulozik et al., J. Clin. Invest. 86:917, 1990).

The use of TGF-β and TGF-β antagonists to modulate blood pressure is disclosed in PCT/US91/0449 published on Dec. 26, 1991. Recombinant TGF-β obtained from Chinese Hamster Ovary cells was reported to induce rapid, significant, and sustained decreases in arterial blood pressure of cynomolgus monkeys receiving daily injections of the recombinant molecule.

The DPP/VGl family includes the bone marrow morphogenetic proteins (BMPs), termed BMP1 through BMP7, DPP and Vgl. The BMPs are osteoinductive agents present in adult bone. They are potent initiators of new bone formation and they appear to act on mesenchymal progenitor cells, directing their differentiation into both cartilage and bone-forming cells. It has also been suggested that they play an important role during embryonic skeleton formation (See Review by Rosen and Thies, in Trends in Genetics, 8(3)97, 1992 and references therein). Decapentaplegic (DPP) plays a fundamental role in dorsoventral body patterning and in imaginal disk formation in Drosophila (Padgett et al., 1987, Nature, 325:81–84). Vgl is involved in embryonic development in *Xenopus laevis*.

The inhibin family includes the activins and inhibins. The activins are involved in the regulation of numerous biological processes. For example, they are involved in the proliferation of many tumor cell lines, the control of secretion and expression of the anterior pituitary hormones (EG, FSH, GH, and ACTH), neuron survival, hypothalamic oxytocin secretion, erythropoiesis, placental and gonadal steroidogenesis early embryonic development and the like. Inhibin molecules also help to regulate erythropoiesis and modulate the release of FSH (Mason et al., 1985, Nature 318:659–663 and Ling et al., Nature 321:779, 1986).

The Mullerian Inhibiting Substance family includes Mullerian Inhibiting Substance (MIS) which is an important morphogenetic signal in developing reproductive systems of mammalian embryos (Cate et al, Cell 45:685–698).

The members of the TGF-$\beta$ superfamily may mediate signal transduction through families of related receptors. The cell surface receptors for TGF-$\beta$ and activin are composed of type I and type II receptor chains, both of which contain a cysteine rich extracellular domain and a cytosolic serine/threonine protein kinase domain. The type I and type II receptors form heterodimers which appears to be necessary for cytokine-dependent intracellular signalling (Massague, Cell, 69:1067, 1992 and references therein, and Lin et al., Cell 68:775, 1992).

TGF-$\beta$ binding proteins have been identified which do not function as signalling receptors. The proteoglycan betaglycan is the most widely distributed TGF-$\beta$ binding protein after receptors I and II. Betaglycan is a membrane anchored proteoglycan that binds TGF-$\beta$ via the core protein and it has been suggested that betaglycan acts as a receptor accessory molecule in the TGF-$\beta$ systems (Massague, Cell, 69:1067, 1992 and references therein).

A number of other extracellular matrix proteins have been shown to bind TGF-$\beta$, including decorin, biglycan, thrombospondin and the serum glycoprotein $\alpha$2-macroglobulin (Y. Yamaguchi, D. M. Mann, E. Ruoslahti, Nature 346, 281 (1990); S. Scholtz-Cherry J. E. Murphy-Ullrich, *J. Cell Biol.* 122, 923 (1993); O'Conner-McCourt, L, M. Wakefield *J. Biol. Chem.* 262, 14090 (1987); and J. Massague *Curr. Biol.* 1, 117 (1991)). Thrombospondin has been shown to bind and activate latent TGF-$\beta$, but does not neutralize cytokine activity. In contrast, decorin has been shown to neutralize the anti-proliferative activity of TGF-$\beta$ (Yamaguchi et al., Nature 346:281, 1990). Decorin has also been found to antagonize the action of TGF-$\beta$ in vivo using an experimental glomerulonephritis model (Border et al., Nature 360:361, 1992).

Bovine fetuin, is one of the first glycoproteins to be purified from fetal calf serum (FCS). Fetuin is analogous to human $\alpha$-2 HS-glycoprotein ($\alpha$2-HS) which is believed to be produced by the liver (Kellerman et al. J. Biol. Chem. 264:14121, 1989). Fetuin has been shown to promote cell growth in vitro without any known cell surface receptor (B. T. Puck, C. A. Waldren, C. Jones, Proc. Natl. Acad. Sci. U.S.A. 59, 192 (1968), and it has been shown to be a negative acute phase reactant (J. P. Lebreton, F. Joisel, J. P. Raoult, B. Lannuzel, J. P. Rogez, et al, J. Clin. Invest. 64, 118 (1979). M. Daveau, C. Davrinche, N. Djelassi, J. Lemetayer, N. Julen, et al, FEBS Lett. 273, 79 (1990)). Serum fetuin accumulates in bone (I. R. Dickson, A. R. Poole, A. Veis, Nature 256, 430 (1975), J. T. Triffitt, U. Gebauer, B. A. Ashton, M. E. Owen, Nature 262, 226 (1976), G. Rauth, O. Pöschke, E. Fink, M. Eulitz, S. Tippmer, et al, Eur. J. Biochem. 204, 523 (1992)) with highest concentrations found during bone growth. It also enhances bone resorption in cultured bone explants in vitro (G. C. Colclasure, W. S. Lloyd, M. Lamkin, W. Gonnerman, R. F. Troxler, et al, J. Clin. Endocrin. Metabolism 66, 187 (1988), and increases adipogenesis (A. J. Cayatte, L. Kumbla, M. T. R. Subbiah, J. Biol. Chem 265, 5883 (1990)). Inflammation is associated with significantly reduced serum fetuin concentrations (J. P. Lebreton, F. Joisel, J. P. Raoult, B. Lannuzel, J. P. Rogez, et al, J. Clin. Invest. 64, 118 (1979). M. Daveau, C. Davrinche, N. Djelassi, J. Lemetayer, N. Julen, et al, FEBS Lett. 273, 79 (1990)). Serum fetuin concentrations are also depressed in patients with Paget's disease, an affliction of increased bone turnover which leads to disordered and thickened bone (B. A. Ashton, R. Smith, Clin. Sci. 58, 435 (1980)). In a subset of osteogenesis imperfecta patients, the loss of bone is associated with elevated serum fetuin levels.

The cDNA sequence encoding the bovine fetal protein fetuin has been reported (K. M. Dziegielewska et al., J. Biol. Chem. 265:4254, 1990). The deduced amino acid sequence indicates that the protein is a single chain preceded by a signal sequence. The sequence of fetuin shows over 70% similarity to human $\alpha_2$HS glycoprotein.

Decorin is a small chondroitin-dermatan sulphate proteoglycan consisting of a core protein and a single glycosaminoglycan chain. The expression of high levels of decorin in Chinese hamster ovary cells has a dramatic effect on their morphology and growth properties and this effect has been attributed in part to the ability of decorin to bind transforming growth factor-$\beta$ (Y. Yamaguchi et al., Nature 346:281, 1990). The administration of decorin has been found to inhibit the increased production of extracellular matrix and attenuate manifestations of glomerulonephritis in an experimental glomerulonephritis model (W. A. Border, Nature 360:361, 1992).

SUMMARY OF THE INVENTION

The present inventors have found that fetuin Sound to and antagonized the antiproliferative activity of TGF-$\beta$, and it was able to inhibit the anti-proliferative activity of TGF-$\beta$ in a dose dependent manner. The present inventors also demonstrated that the action of fetuin as an antagonist of TGF-$\beta$ in tissue culture was due to binding of the two proteins. By using surface plasmon resonance which allows the visualisation of macromolecular interactions in real time, it was shown that fetuin could physically bind to TGF-$\beta$1. Petuin was also found to bind to the closely related cytokine TGF-$\beta$2 with similar affinity. Fetuin also bound with highest affinity to bone morphogenic proteins, including immobilized BMP-2, BMP-4 and BMP-6. BMP-2 showed the highest affinity for fetuin and fetuin was found to suppress BMP-2 mediated bone differentiation in vitro.

Furthermore, the present inventors have significantly defined a binding domain common to fetuin and TGF-$\beta$ receptor type II designated TGF-$\beta$ Receptor II Homology 1 domain (TRH1), which mediates their binding to cytokines of the TGF-$\beta$ superfamily. The domain is defined by two disulphide loops which are designated a and b in FIGS. 6 to 8.

Other proteins such as bovine thyroglobulin were found to contain the TRH1 domain. Thyroglobulin was found to bind to the cytokines BMP-2, BMP-4, TGF-$\beta$1 and TGF-$\beta$2 with a higher affinity than fetuin. Thyroglobulin was also found to neutralize TGF-$\beta$1 activity in a growth inhibition assay.

The present inventors also found that ligand binding and ligand specificity was mediated by the TRH1b sequence within the TRH1 domain (See FIGS. 6 and 7 and the Sequence Listing SEQ. ID. NOS. 5 to 7). Synthetic disulphide-looped peptides corresponding to this domain in fetuin and TRH1 bound directly to BMP-2 and TGF-β1 with the same specificity reflecting that of the native proteins. The TRH1 domain and the TRH1b subdomain have not been found in compounds which have previously been shown to bind to members of the TGF-β superfamily and neutralize their activity, for example, decorin.

The finding that fetuin and thyroglobulin complex with cytokines of the TGF-β superfamily through sequences within the TRH1 domain, and that they are antagonists of these cytokines, allows the identification of substances which modulate cytokines of the TGF-β superfamily, and which accordingly may be used in the treatment of conditions requiring modulation of TGF-β superfamily cytokines.

Therefore, the present invention relates to a method for assaying for the presence of a substance that modulates a cytokine of the TGF-β superfamily which comprises (a) reacting a substance which is suspected-of modulating a cytokine of the TGF-β superfamily with a TGF-β binding compound which is not a TGF-β receptor and which contains a TRH1 domain, or a portion, or a mimetic thereof, and a cytokine of the TGF-β superfamily, under conditions where the TGF-β binding compound, portion, or mimetic thereof, and the cytokine are capable of forming a complex, the TGF-β binding compound, portion or mimetic thereof, A-and/or the cytokine being present in a known concentration, (b) assaying for complexes, free TGF-β binding compound, portion or mimetic thereof, and/or cytokine, and (c) comparing with a control.

The present invention further relates to the use of a TGF-β binding compound which is not a TGF-β receptor and which contains a TRH1 domain, for modulating cytokines of the TGF-β superfamily. In particular, the invention relates to the use of these compounds for the treatment of conditions requiring modulation of cytokines of the TGF-β superfamily. The compound may be introduced directly into an individual, or it may be produced indirectly by expression of a gene encoding the TGF-β binding compound.

Therefore, the invention relates to a pharmaceutical composition comprising at least one TGF-β binding compound which is not a TGF-β receptor and which contains a TRH1 domain, or a portion, or a mimetic thereof, and a pharmaceutically acceptable carrier, auxiliary or excipient. The composition may be used as an antagonist of TGF-β superfamily cytokines and therefore will be useful in the treatment of conditions requiring modulation of TGF-β superfamily cytokines.

The invention also relates to a pharmaceutical composition comprising a recombinant molecule containing a gene encoding at least one TGF-β binding compound which is not a TGF-β receptor and which contains a TRH1 domain, or a portion, or a mimetic thereof.

The invention also contemplates a method of treating a subject suffering from a condition requiring modulation of cytokines of the TGF-β superfamily comprising administering an effective amount of a TGF-β binding compound which is not a TGF-β receptor and which contains a TRH1 domain, or a portion, or a mimetic thereof, or a substance identified by the methods of the invention.

The invention also contemplates a method of enhancing in an individual the activity of a growth factor whose effects are overridden by a cytokine of the TGF-β superfamily comprising administering to the individual a composition of the invention, or a substance which is an antagonist of cytokines of the TGF-β superfamily identified in accordance with the methods of the invention.

Still further the invention contemplates a method for assaying for a cytokine of the TGF-β superfamily in a sample comprising (a) reacting a sample suspected of containing the cytokine with a definite quantity of a TGF-β binding compound which is not a TGF-β receptor and which contains a TRH1 domain, or a portion, or a mimetic thereof, and a definite quantity of the cytokine, under conditions where the compound and the cytokine are capable of forming a complex, the compound and/or the cytokine being present in a known concentration, (b) assaying for complexes, free compound and/or cytokine, and (c) comparing with a control.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will now be described in relation to the drawings in which:

FIG. 6 is a multiple alignment of fetuin sequences from bovine, pig, sheep, rat and human;

FIG. 8 is an alignment of the fetuin and TβRII sequences;

FIG. 11 shows the sequence of the TGF-β type II receptor;

DETAILED DESCRIPTION OF THE INVENTION

As hereinbefore mentioned, the present invention relates to a method for assaying for the presence of a substance that modulates cytokines of the TGF-β superfamily. A substance which is suspected of modulating cytokines of the TGF-β superfamily is reacted with a TGF-β binding compound which is not a TGF-β receptor and which contains a TRH1 domain, or a portion, or a mimetic thereof, and a cytokine of the TGF-β superfamily. Suitable reaction conditions are employed to permit formation of a complex between the compound and the cytokine. The compound and/or the cytokine are present in a known concentration. The complexes, free compound and/or cytokine are assayed and the results are compared with a control.

"Cytokines of the TGF-β superfamily", "Members of the superfamily of TGF-β of cytokines", or "TGF-β superfamily cytokines" referred to herein includes cytokines having the structural characteristics of the members of the TGF-β superfamily. The structural prototype for the gene superfamily is TGF-β. TGF-β is produced as a precursor which is characterised by having an N-terminal hydrophobic signal sequence for translocation across the endoplasmic reticulum, a pro-region, and a C-terminal bioactive domain. Prior to release from the cell, the pro-region is cleaved at a site containing four basic amino acids immediately preceding the bioactive domain (Massague, 1990).

Figure 2:
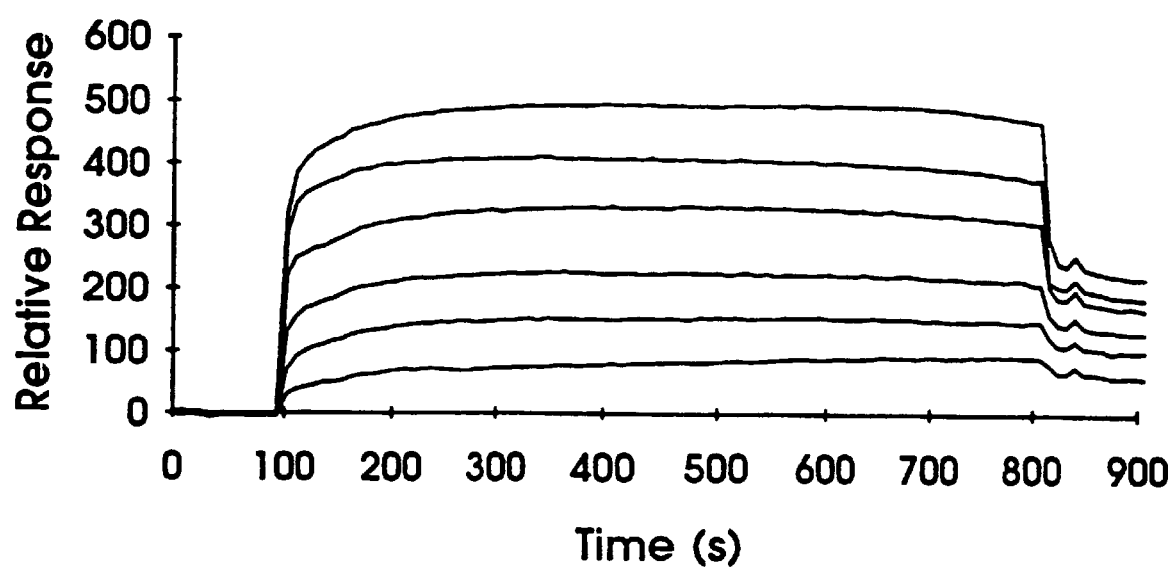
FIG. 2 is a sensorgram overlay plot showing bovine fetuin binding in response units (R.U.) to immobilized TGF-β1.

The precursor structure of TGF-β is shared by members of the TGF-β superfamily cytokines, with the exception of the TGF-β4 precursor which lacks a distinguishable signal sequence. The degree of identity between family members in the C-terminal bioactive domain is from 25 to 90% (See Basler et al. Cell, 73:687, 1993, FIG. 2). At least 7 cysteines are conserved in the bioactive domain in all members of the superfamily and all nine cysteines are conserved in the TGF-β family and the inhibin β chains. With the exception of Mullerian Inhibiting Substance (MIS) (Cate et. al., 1986), the bioactive domain is cleaved to generate a mature monomer.

Examples of cytokines of the TGF-β superfamily include the cytokines of the TGF-β family, the inhibin family, the DPP/VGl family and the Mullerian Inhibiting Substance Family.

The TGF-β family includes five members, termed TGF1 through TGF-β5, all of which form homodimers of about 25 kd (reviewed in Massague, 1990). The family also includes TGF-β1.2 which is a heterodimer containing a β1 and a β2 submit linked by disulfide bonds. The five TGF-β genes are highly conserved over great evolutionary distances. The mature processed cytokines produced from the members of the gene family show almost 100% amino acid identity between species, and the five peptides as a group show about 60–80% identity.

The DPP/VGl family includes the six BMPs termed BMP-2 through BMP-7, Vgl, and DPP. BMPs are 30–40% homologous to members of the TGF-β family. BMP2–7 share considerable homology with members of the Inhibin family which includes the inhibins/activins. The inhibins are composed of an α subunit, and either a βA subunit (inhibin A), or a βB subunit (inhibin B). The amino acid identity of the two β subunits is about 60% while the e subunit sequence is very divergent (about 25% identity). The family includes inhibin A (α·βA dimer), inhibin B (α·βB dimer), activin A (βA homodimer), and activin AB (βA·βB dimer) (See Massague, 1990, and Rose, V. and R. S. Thies, 1992, for reviews on the DPP/VGI family and in particular BMP's).

The Mullerian Inhibiting Substance Family includes the Mullerian Inhibiting Substance (MIS) homodimer. The deduced sequence of the MIS C-terminal domain is about 25% identical to that of the other members of the superfamily. MIS is a disulfide-linked homodimer of 70–74 kd glycosylated chains that contains the glycosylated N-terminal extension uncleaved from the C-terminal domain (See review by Massague, 1990, and references referred to therein).

Preferably, the methods and compositions described herein incorporate members of the TGF-β family and the DPP/VGl family, most preferably TGF-β1, TGF-β2, BMP-2, BMP-4 and BMP-6.

Cytokines of the TGF-β superfamily can be isolated from natural or recombinant sources. For example, TGF-β1 may be synthesized by a variety of normal and transformed cells in culture (Roberts et al., 1981, Proc. Natl. Acad. Sci. U.S.A. 78:5339–5343) and it has been purified from placenta (Frolik et al., 1983, Proc. Natl;. Acad. Sci. U.S.A. 80:3676–3680), kidney (Roberts et al., 1983, Biochemistry 22:5692–5698), urine (Twardzik et al., 1985, J. Cell. Biochem. 28:289–297) and blood platelets (Childs et al., 1982, Proc. Natl;. Acad. Sci. U.S.A. 79:5312–5316). BMP-2, -3, 6 and 7 may be isolated from human and/or bovine bone.

Large quantities of the cytokines may be obtained by recombinant techniques using host cells transfected with recombinant vectors containing the coding sequence for the cytokine. The cytokines may also be obtained from commercial sources. (For example, TGF-β1 may be obtained from Collaborative Research, Bedford, Mass.).

The TGF-β binding compound used in the methods and compositions described herein may be a glycoprotein or polypeptide. The compound binds to a cytokine of the TGF-β superfamily, preferably TGF-β1, with a $K_D$ of greater than $10^{-5}$, and/or neutralizes the activity of a TGF-β cytokine such as TGF-β1 or BMP-2 in a growth inhibition assay-as described herein. The TGF-β binding compound is not a natural target TGF-β receptor namely a type I or type II receptor of TGF-β or activin which contain a cytosolic serine/threonine protein kinase domain. The sequence of the TGF-β type II receptor is set out in FIG. 11 and in the Sequence Listing as SEQ. ID. NO. 1.

The protein portion of the TGF-β binding compound contains at least one amino acid sequence of the TRH1 domain, or a portion or a mimetic thereof. The TRH1 domain comprises a region about 43 amino acids in length, containing two disulfide loops designated a and b in FIGS. 7 and 8. A TRH1 domain may be identified using the GCG routine "findpatterns" and the following pattern: CX{8,14}(N,Q)X{12,16}CX{4,5}(K,R)X{2,6}(S,T)X{4,9} CX{0, 2}DX{5,6}(D,E) (See Example 3 herein). The TRH1 domain from fetuin is shown in the Sequence Listing as SEQ. ID. NO. 2 and in FIG. 8; the TRH1 domain from the TGF-β type II receptor is shown in the Sequence Listing as SEQ. ID. NO. 3 and in FIG. 8; and, the TRH1 domain from thyroglobulin is shown in the Sequence Listing as SEQ. ID. NO. 4 and in FIG. 8. Preferably, the compound contains a portion of the TRH1 domain having the amino acid sequence of the TRH1b subdomain which contains about 18–20 amino acids. A TRH1b subdomain may be identified using the GCG routine "findpatterns" and the following pattern: CX{4,5}(K,R)X{2,6}(S,T)X{4,9}CX{0,2}DX{5,6}(D,E), or CX{0,1}(V,I,F,Y)X{1,3}(V,W,L)X{0,1}(K,R)X{45} (V,I,F)X{1,2}(L,I)X{2,4}CX{0,2}D. The TRH1b subdomain from fetuin, the TGF-β type II receptor, and thyroglobulin are shown in the Sequence Listing as SEQ. ID. NOS. 5, 6, and 7, respectively, and in FIG. 7. It will be appreciated that the terminal amino acids shown in SEQ. ID. NOS. 5, 6, and 7 may be removed to provide an 18–19 TRH1b peptide.

Examples of TGF-β binding compounds which may be used in the methods and compositions of the invention are fetuin, including human fetuin also known as β-$_2$-HS glycoprotein, thyroglobulin, kininogens (Kellerman et al. Biochem. J. 247:15, 1987), and TRH1b peptides.

The protein portion of the TGF-β binding compound may include sequences which are homologous to the amino acid sequence of the TRH1 domain, or a portion thereof such as the TRH1b subdomain. A sequence which is homologous to the TRH1 domain or a portion thereof such as the TRH1b subdomain is defined as a sequence which has at least about 40% and 70% identity, respectively. A TGF-β binding compound containing a homologous sequence should be capable of binding to a TGF-β cytokine, preferably TGF-β1, with a $K_D$ of greater than $10^{-5}$ and/or neutralizing activity of a TGF-β cytokine such as TGF-β1 or BMP-2 in a growth inhibition assay as described herein.

It will be appreciated that a TGF-β binding compound may be modified by substituting amino acids for like amino acids. For example, a basic amino acid may be substituted with a different basic amino acid, or a hydrophobic amino acid may be substituted with a different hydrophobic amino acid in the TRH1 domain or TRH1b subdomain.

Mimetics of the TGF-β binding compounds may also be used in the methods and compositions of the invention. The term "mimetic" refers to compounds which have a related three dimensional structure i.e. compounds which have one or both of the characteristic disulfide loop structures as shown schematically in FIG. 7, preferably the loop structure designated "b". The selection of mimetics may be done using methods such as described in for example P. S. Farmer, in Drug Design, EJ Ariens, Ed. (Academic Press, New York, 1980) Vol. 10, p.119–143; Ball J. B., P. F. Alewood, J. Mol. Recognition 3,55, 1990; B. A. Morgan and J. A. Gainer, Annu. Rep. Med. Chem. 24, 243, 1989; and R. M. Friedinger, Trends Pharmacol. Sci. 10, 270 1989.

A TGF-β binding compound may also be a chimeric molecule. For example, the TRH1b region of fetuin (SEQ. ID. NO. 5 and Cys 26 to Cys 44 in SEQ. ID. NO. 2) can be replaced by the corresponding loop from the TGF-β type II receptor (SEQ. ID. NO. 6 and Cys 24 to Cys 41 in SEQ. ID. NO. 3).

TGF-β binding compounds such as fetuin and thyroglobulin may be obtained using conventional isolation and purification techniques. For example, the compounds may be obtained by ammonium sulfate fractionation of fetal calf serum followed by gel filtration chromatography. They may also be obtained from commercial sources (e.g. Sigma, St. Louis, Mo., U.S.A.). TGF-β binding compounds may also be synthetically constructed using conventional methods such as chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

A TGF-β binding compound, and portions thereof, including the TRH1 domain and TRH1b subdomain, may also be expressed in a host cell including bacteria, yeast, insect or mammalian cells, or animals using methods well known in the art (see, for e.g., Itakura et al., U.S. Pat. No. 4,704,362; Hinnen et al., PNAS U.S.A. 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel, et al., U.S. Pat. No. 4,766,075; and Sambrook et al. Molecular Cloning A Laboratory Manual, 2nd edition, Cold Spring Harbor Laboratory Press, 1989).

Preferably, the expression system is a mammalian expression system. For example, Chinese Hamster Ovary (CHO) cells may be used to produce a correctly folded and glycosylated fetuin or chimeric fetuin, and to permit recovery of the protein from serum-free cell culture supernatants. Both a transient and stable approach may be used. The former approach may be based on the SFU virus replicon which can be used to quickly produce relatively large amounts of recombinant protein. The stable approach may employ the well characterized cytomegalovirus (CMV) promoter which allows for a more permanent and constant source of the protein. The coding region of a cDNA encoding the protein can be cloned out of a cDNA library using the polymerase chain reaction (PCR) amplification techniques (Mullis el al., U.S. Pat. No. 4,863,195 and Mullis, U.S. Pat. No. 4,683,202). The nucleotide sequence may be confirmed by DNA sequencing. A PCR based cloning strategy will allow introduction of convenient restriction sites for subcloning into the expression vectors.

A TGF-β binding compound, and portions thereof including the TRH1 domain and TRH1b subdomain may be expressed in non-human transgenic animals such as, rats, mice, rabbits, sheep and pigs (see Hammer et al. (Nature 315:680–683, 1985), Palmiter et al. (Science 222:809–814, 1983), Brinster et al. (Proc Natl. Acad. Sci U.S.A. 82:44384442, 1985), Palmiter and Brinster (Cell. 41:343–345, 1985) and U.S. Pat. No. 4,736,866).

It will be appreciated that the selection of the TGF-β binding compound and the TGF-β superfamily cytokine in the method of the invention will depend on the nature of the substance to be assayed. It will also be appreciated that the selection of the compound and TGF-β superfamily cytokine in the method of the invention will allow for the identification of a specific substance that affects a specific interaction. Thus, the identification of the specific site of binding of the TRH1 domain to TGF-β superfamily cytokines by the present inventors allows the identification of specific substances that modulate TGF-β superfamily cytokines.

Conditions which permit the formation of cytokine-TGF-β binding compound complexes may be selected having regard to factors such as the nature and amounts of the cytokine and the TGF-β binding protein.

The complexes, and free compounds and cytokines in the methods of the invention may be isolated by conventional isolation techniques, for example, salting out, chromatography, electrophoresis, gel filtration, fractionation, absorption, polyacrylamide gel electrophoresis, agglutination, or combinations thereof.

The complexes or free compounds or cytokines may be assayed using known methods. To facilitate the assay of the components, antibody against the compound or cytokine which may be labelled, or a labelled compound or cytokine may be utilized. The components may also be assayed by determining the ability to neutralize activity of a TGF-β cytokine such as TGF-β1 or BMP-2 in a growth inhibition assay as described herein.

As controls, the methods of the invention may be carried out in the absence of the substance which is suspected of modulating cytokines of the TGKβ superfamily, or in the presence of a substance which is known to modulate cytokines of the TGF-β superfamily.

The TGF-β binding compounds and TGF-β superfamily cytokines may be used to prepare antibodies and the antibodies may be used to facilitate isolation and separation of complexes and free compound, or cytokine. As described below, antibodies to the TRH1 domain and portions thereof may also be used to neutralize the activity of a TGF-β cytokine by blocking its binding to its native receptor, and accordingly they may allow therapeutic intervention in cases where there is excessive TGF-β cytokine activity such as cases of fibrosis, or where TGF-β serves as an autocrine growth factor for tumors. They may also be used for assaying for the presence of a TGF-β superfamily cytokine in a biological sample in specific diagnostic applications.

Within the context of the present invention, antibodies are understood to include monoclonal antibodies, polyclonal antibodies, antibody fragments (e.g., Fab, and F(ab')$_2$ and recombinantly produced binding partners.

Polyclonal antibodies may be readily generated by one of ordinary skill in the art from a variety of warm-blooded animals such as horses, cows, various fowl, rabbits, mice, or rats. The present inventors have immunized rabbits with a TRH1b peptide and obtained an animal which displays clinical symptoms similar to those found with autoimmune conditions. In particular, the rabbits showed fibrosis of their foot pads, and there was evidence of inflammatory responses in the liver.

Monoclonal antibodies may also be readily generated using conventional techniques (see U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference). Binding partners may also be constructed utilizing recombinant DNA techniques to incorporate the variable regions of a gene which encodes a specifically binding antibody (See Bird et al., Science 242:423–426, 1988).

Antibodies specific for some of the cytokines may also be obtained from commercial sources. For example, antibodies to cytokines of the TGF-β family may be obtained from American Diagnostics Inc., Conn. U.S.A., Oncogene Science, N.Y., U.S.A., and Dimension Laboratories, Mississauga, Canada.

The antibodies against the compound or cytokines may be labelled using conventional methods with various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive phosphorous $^{32}$P, iodine $I^{25}$, $I^{131}$ or tritium. Antibodies specific for the compound or cytokine may also be coupled to electron dense substances, such as ferritin or colloidal gold, which are readily visualised by electron microscopy.

The TGF-β binding compound or cytokine used in the method of the invention may be insolubilized. For example, they may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized compound or cytokine may be prepared by reacting the material with a suitable insoluble carrier using known chemical or physical methods, for example, cyanogen bromide coupling.

The methods of the invention may be used to assay for a substance that modulates TGF-β superfamily cytokines preferably a suspected agonist or antagonist. Generally, an antagonist may constitute any molecule with similar binding activity to a TGF-β superfamily cytokine but incapable of propagating the biological response normally induced by the cytokine. An antagonist may also be a molecule that mimics the binding site on the receptor for the cytokine. For example, an antagonist constitutes a molecule containing the TRH1 domain, and in particular the TRH1b subdomain. As described in detail herein compounds, such as fetuin and thyroglobulin which contain the TRH1 domain (and the TRH1b subdomain) are antagonists of cytokines of the TGF-β superfamily. On the other hand, an agonist constitutes a molecule which binds to the specific binding site on the receptor for the cytokine i.e. the TRH1 domain or the TRH1b subdomain, in some advantageous manner compared to the natural cytokine. The agonist or antagonist may be an endogenous physiological substance or it may be a natural or synthetic drug.

The invention also relates to a pharmaceutical composition comprising at least one TGF-β binding compound. The invention also contemplates pharmaceutical compositions containing substances identified using the methods described herein. The pharmaceutical compositions may be used as an agonist or antagonist of the interaction of a TGF-β cytokine and a TβRII. The composition preferably contains fetuin, more preferably human fetuin, also known as α-2 HS-glycoprotein, or a chimeric fetuin as described herein. Fetuin is particularly suitable as a pharmacological agent since it is a natural human compound which is non-immunogenic, and it can be produced as a recombinant molecule as described herein.

The pharmaceutical compositions of the invention contain at least one TGF-β binding compound, or substance identified using the methods of the invention, alone or together with other active substances. Such pharmaceutical compositions can be for oral, topical, rectal, parenteral, local, inhalant or intracerebral use. They are therefore in solid or semisolid form, for example pills, tablets, creams, gelatin capsules, capsules, suppositories, soft gelatin capsules, gels, membranes, tubelets. The compositions of the invention may also be conjugated to transport molecules such as transferrin to facilitate transport of the composition across the blood brain barrier.

The pharmaceutical composition of the invention may also contain additional therapeutic compounds. For example, glucocorticoids which are widely used in the treatment of many conditions including rheumatoid arthritis, chronic active hepatitis, and asthma may be included in the pharmaceutical compositions of the invention.

The pharmaceutical compositions of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance ( s) is combined in a mixture with a pharmaceutically acceptable vehicle. Suitable vehicles are described, for example, in Remington's Pharmaceutical Sciences (Remington's Pharmaceutical Sciences, sack Publishing Company, Easton, Pa., U.S.A. 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids.

The invention also relates to a composition comprising a recombinant molecule containing a gene encoding at least one TGF-β binding compound which is not a TGF-β receptor and which contains the TRH1 domain, or a portion, or a mimetic thereof. The recombinant molecule also contains suitable transcriptional or translational regulatory elements. Suitable regulatory elements may be derived from a variety of sources, and they may be readily selected by one of ordinary skill in the art. Examples of regulatory elements include: a transcriptional promoter and enhancer or RNA polymerase binding sequence, a ribosomal binding sequence, including a translation initiation signal. Additionally, depending on the vector employed, other genetic elements, such as selectable markers, may be incorporated into the recombinant molecule. The recombinant molecule may be introduced into cells of a subject using in vitro delivery vehicles such as retroviral vectors, adenoviral vectors and DNA virus vectors. They may also be introduced into such cells in vivo using physical techniques such as microinjection and electroporation or chemical methods such as coprecipitation and incorporation of DNA into liposomes. The compositions may also be delivered in the form of an aerosol or by lavage.

The present invention also provides for methods in which a patient suffering from a condition requiring modulation of cytokines of the TGF-β superfamily is treated with an effective amount of a TGF-β binding compound. Therapeutic methods comprising administering agonists or antagonists identified with the methods of the present invention are also within the scope of the present invention.

The TGF-β binding compounds, substances identified using the method of the invention, antibodies, and compositions containing same, may be used in a variety of applications. Since the TGF-β cytokines are involved in many biological processes, the compounds, substances, antibodies and compositions can be applied to the modulation of these processes.

Agonists of cytokines of the TGF-β family identified using the method of the invention may be used for example, to stimulate wound healing, to suppress the growth of TGF-β sensitive tumors, to suppress the immune response, and to stimulate angiogenesis. The immune response may be suppressed in transplant cases to reduce the rejection of the transplanted organ.

Antagonists of cytokines of the TGF-β family can be used to block the binding of an endogenous TGF-β to its natural target receptors thereby blocking cell proliferative or inhibitory signals generated by the ligand-receptor binding event. Antagonists such as TGF-β binding compounds and antibodies would thereby stimulate immune responses and reduce the deposition of extracellular matrix. Accordingly, antagonists would be particularly suitable for the treatment of conditions such as fibrosis including pulmonary fibrosis, fibrosis associated with chronic liver disease, hepatic venoocclusive and idiopathic interstitial pneumonitis, kidney disease, and radiotherapy or radiation accidents; proliferative vitreoretinopathy; systemic sclerosis; autoimmune disorders such as rheumatoid arthritis, Graves disease, systemic lupus erythematosus, Wegener's granulomatosis, sarcoidosis, polyarthritis, pemphigus, pemphigoid, erythema multiforme, Sjogren's syndrome, inflammatory bowel disease, multiple sclerosis, myasthenia gravis keratitis, scleritis, Type I diabetes, insulin-dependent diabetes mellitus, Lupus Nephritis, and allergic encephalomyelitis; proliferative disorders including various forms of cancer such as leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, arthrosclerosis, angiogenesis, and viral infections, in particular HIV infections.

Antagonists of cytokines of the TGF-β family may also be used to elevate blood pressure through the inhibition of hypotension induced by TGF-β. Methods which lower and/ or maintain the level of circulating TGF-β in a subject may result in a similar pressor effect and may prevent excessive hypotensive signal generation and resulting hypotension.

The stimulation of FSH release by activin can be enhanced by the administration of a specific TGF-β binding compound. The compound would prevent the formation of a complex between activin and its natural receptor which would then act to stimulate the release of FSH. Therefore, the TGF-β binding compound would reduce the effect of activin by blocking the normal interaction between activin and activin receptor. Accordingly, the TGF-β binding compound can be applied to the control of fertility in humans, domesticated animals, and animals of commercial interest. The action of activin on erythropoiesis can also be modulated by administering a modulating effective amount of a TGF-β binding compound. The compounds, substances, antibodies and compositions of the invention can also be used in the diagnosis and/or treatment of activin-dependent tumors or for enhancing the survival of brain neurons.

The present inventors' work supports a role for fetuin and TGF-β superfamily cytokine interactions in bone cell differentiation. The present inventors have found that fetuin has a greater affinity for BMPs, and fetuin and BMPs are known to be co-localized in developing bone. The present inventors have also shown that fetuin suppresses BMP-2 dependent bone differentiation in vitro. Therefore, substances that modulate TGF-β superfamily cytokines, in particular BMP-2 to BMP-7, identified herein and using the methods of the invention may be used to induce bone formation, and for example, they can be used to repair or heal fractures, treat osteoporosis, address dental problems, and they may be used with implants to encourage bone growth.

TGF-β has been found to control proliferation and differentiation of several cell types specific to bone including mesenchymal precursor cells, chondrocytes, osteoblasts and osteoclasts. TGF-β has been shown to block the differentiation of normal rat diploid fetal osteoblasts in vitro (E. C. Breen et al. J. Cell. Physiol. 160:323–335, 1994). The effect is restricted to the proliferative phase of the culture before the cells express the mature osteoblastic phenotype. The present inventors have shown that fetuin stimulated cell growth during the proliferative phase, and it inhibited deposition of calcium-containing matrix i.e. bone tissue, following the proliferative phase. Therefore, bone formation (in particular for the applications discussed above) may be stimulated by modulating the early effects of TGF-β cytokines by administering a TGF-β binding compound, and/or by modulating the late effects of the TGF-β cytokines by administering an agonist of a TGF-β cytokine identified using the methods described herein. Disorders where there is too much bone formation (for example, achondroplasia, Paget's disease, and osteopetrosis) may also be treated by modulating TGF-β cytokines using TGF-β binding compounds, and substances identified using the methods of the invention.

TGF-β binding compounds and substances identified using the methods of the invention, may also be used in conjunction with glucocorticoids which are used in the treatment of many diseases including rheumatoid arthritis, chronic active hepatitis, asthma, and in posttransplant tissue rejection. Chronic glucocorticoid therapy has been associated with induced osteoporosis which is a major risk factor for bone loss. TGF-β has been found to play a role in glucocorticoid regulation of bone cell functions (Oursler, M. J. et al, Endocrinology, 133(5), p.2187, 1993).

The utility of the compounds, antibodies, and compositions of the invention may be confirmed in animal experimental model systems. For example, therapeutic utility in fibrotic conditions may be tested by examining the susceptibility of mice to the induction of pulmonary fibrosis by bleomucin sulfate (Baecher-Allan, Regional Immunology 5(3–4):207, 1993). The well-characterized pig model of radiation induced fibrosis described in Martin et al. (Radiation Research 134(1)63, 1993), and the experimental glomerulonephritis model described in Border et al. (Nature 360:361, 1992) may also be utilised. Other models which may be useful in confirming the utility of the compounds, substances and compositions of the present invention include those for wound healing (e.g. the fetal tissue repair model described in Bleacher et al. Dermatologic Clinics 11(4):677, 1993), bone repair (e.g. bone induction in rats - Yasko, A. W., et al., Orthop. Trans. 15:501, 1991; sheep femur - Gerhart T. N. et al, Trans. 37 Annual Meeting Orthop. Res. Soc. Anaheim Calif. Catherson, B., ed) 16(1), p.172, 1991; and dog mandible- Toriumi D. M. et al, Archiv. Otolarynogol. Head Neck Surg. 117:1101–1112, 1991), and autoimmune diseases (e.g. MRL-1 pr/ipr mice are a model for systemic lupus erythematosus, and NZB×NZWf1 mice which demonstrate clinical symptoms comparable to those found with human autoimmune diseases -Theofilopoulos and Dixon, Adv. Immunol. 37, 1985).

It would also be apparent to one skilled in the art that the above described methods, compounds, substances, antibodies, and compositions may be used to study the cytokines of the TGF-β superfamily and, accordingly, will provide further insight into the role of the cytokines in growth, differentiation and morphogenesis.

Cytokines of the TGF-β family arrest the growth of cells thereby overriding the action of other growth factors such as EGF, bFGF, IL-1α, IL-1β, Int-2, keratinocyte growth factor, IL-2, GM-CSF, G-CSF, CNTP, EGF, TGFα, human growth hormone, NGF, PDGF, insulin, IGF-1, IGF-2, bombyxin, glial growth factor TNF, and CD40 ligand (Ewen et al., Cell 74:1009, 1993). For effective use of growth factors in a clinical setting, it would be desirable to reduce the activity of TGF-β cytokines concomitantly.

Accordingly, the invention also contemplates a composition comprising a TGF-β binding compound in combination with a growth factor whose effects are overridden by a cytokine of the TGF-β superfamily. The invention also relates to a method of enhancing treatment of an individual with a growth factor whose effects are overridden by a cytokine of the TGF-β superfamily comprising concomitantly administering with the growth factor a TGF-β binding compound which is not a receptor of TGF-β cytokine and which contains a TRH1 domain. Other antagonists of the binding of cytokines of the TGF-β superfamily identified using the methods of the invention may also be used in these compositions and methods to enhance the activity of growth factors.

Another application of the present invention is the assay of samples for the presence or absence of members of the TGF-β superfamily of cytokines. For example, serum from a patient displaying symptoms related to pathways mediated by members of the superfamily of TGF-β cytokines can be assayed to determine if the observed symptoms are perhaps caused by over-or under-production of such a cytokine. The assays can be carried out in a variety of ways as can readily be identified by one of skill in the art. For example, competitive assays can be employed as well as immunological assays using antibodies of the invention such as radioimmunoassays, ELISA, ERMA, and the like.

In an embodiment of the invention a competitive binding assay is provided for assaying for a cytokine of the TGF-β superfamily in a sample comprising (a) reacting a sample suspected of containing the cytokine with a definite quantity of a TGF-β binding compound which is not a TGF-β receptor and which contains a TRH1 domain or a portion, or a mimetic thereof, and a definite quantity of the cytokine, under conditions where the compound and the cytokine are capable of forming a complex, the compound and/or the cytokine being present in a known concentration, (b) assaying for complexes, free compound and/or cytokine, and (c) comparing with a control.

The method may be used to assay for TGF-β cytokines in tissues and biological samples for example clinical samples of blood, blood product, serum, body fluids, secretions, faeces, washings such as throat washings tissue homogenates and cell culture fluids containing or suspected of containing the cytokines. The cytokines and TGF-β binding compounds which may be used in the method are described in detail above with reference to the method for assaying for substances affecting TGF-β cytokines. Conditions which permit the formation of cytokine-TGF-β binding compound complexes may be selected having regard to factors such as the nature and amounts of the cytokine and the TGF-β binding protein.

The following non-limiting examples are illustrative of the present invention:

EXAMPLES

Example 1

Figure 12:
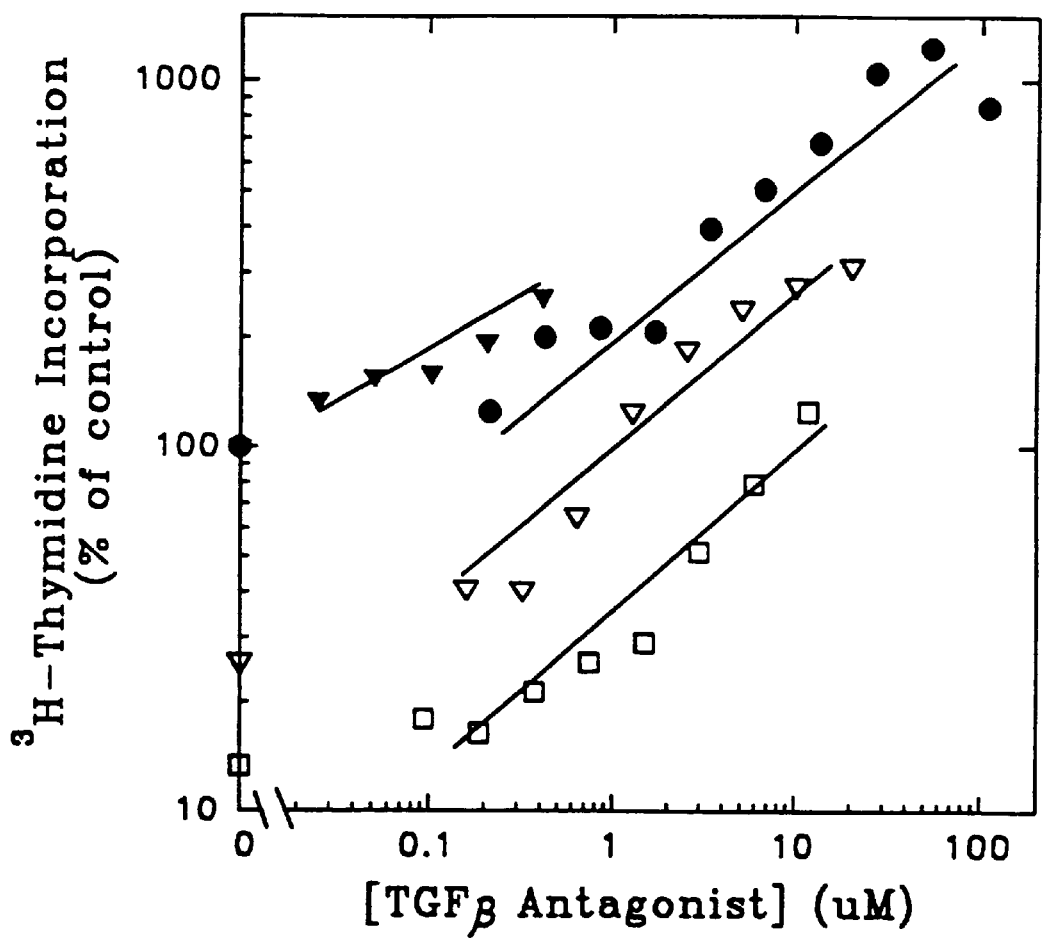
FIG. 12 is a graph showing that bovine fetuin and bovine thyroglobulin neutralize the antiproliferative activity of TGF-β cytokines on cultures of Mv1Lu cells.

The ability of fetuin and thyroglobulin to bind to and antagonize TGF-β cytokines was tested. $^3$H-Thymidine incorporation in Mv1Lu cells, a mink lung epithelial line, was assessed in the presence of TGF-β1 (12 pM) alone, and with increasing concentrations of bovine fetuin (closed circles in FIG. 1); bovine thyroglobulin (open triangles in FIG. 1); or bovine serum albumin (closed triangles in FIG. 1). Fetuin was also titrated into cultures of Mv1Lu cells in the absence (closed circles) or presence of cytokines; 18 pM human TGF-β1 (open squares), or 33 nM human BMP-2 (open triangles) (FIG. 12).

Figure 1:
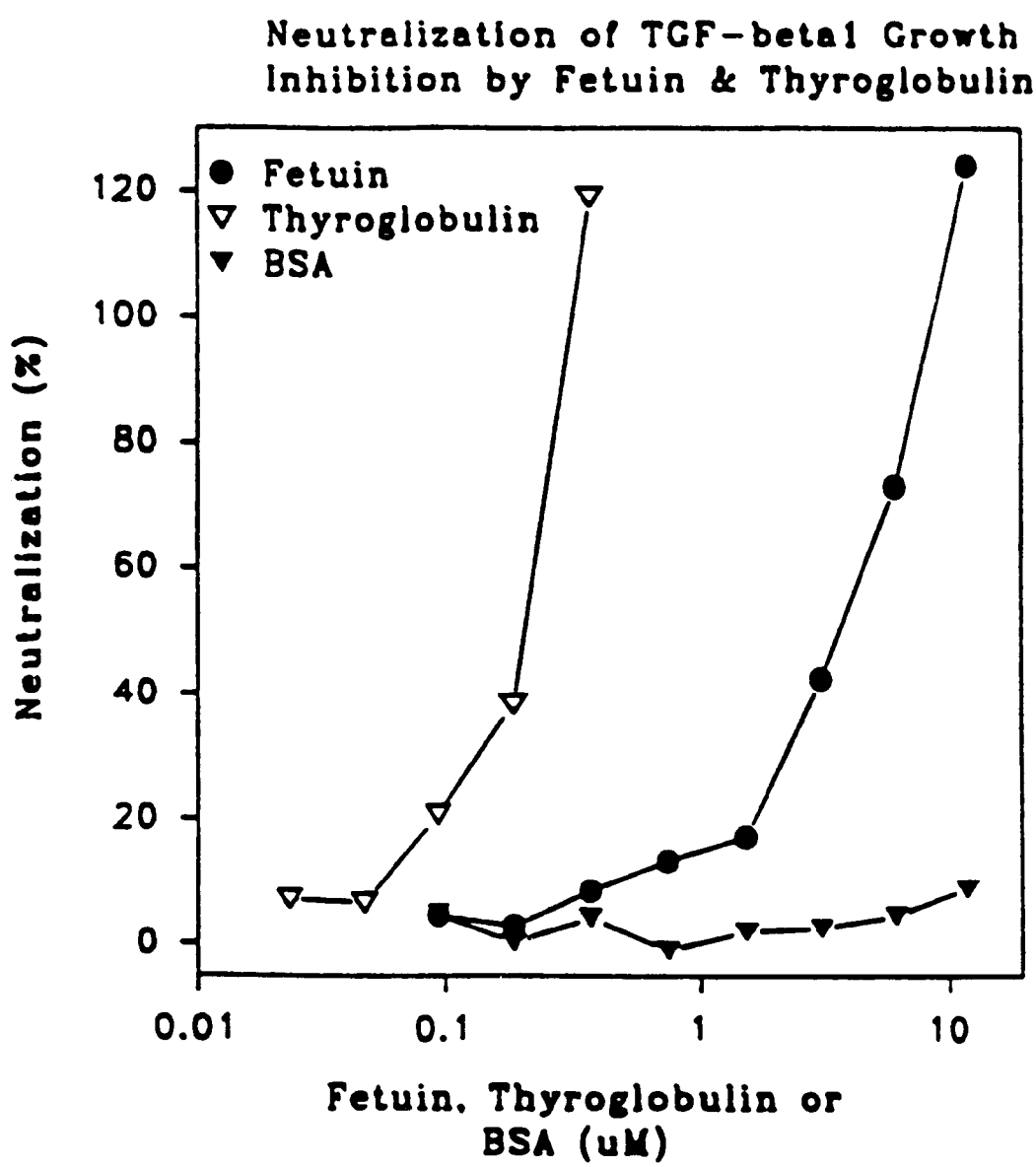
FIG. 1 is a graph showing that bovine fetuin and bovine thyroglobulin neutralize the antiproliferative activity of TGF-β on cultures of Mv1Lu cells.

Mv1Lu cells were seeded at 20,000 cells/well in a 96 well plate containing 0.2% FCS in α-MEM and incubated with the indicated concentrations of proteins for 18 hr. The cells were then pulsed with 8 μCi/ml methyl-$^3$H-thymidine (NEN, Boston, Mass.) for 6 hr. Cells were trypsinized, harvested onto filtermats and counted in a β-Counter. Percent neutralization is defined as incorporation in the presence of 12 pM TGF-β1 alone set at 0%, and incorporation without additions as 100%. The difference in $^3$H-thymidine incorporation between 0% and 100% was 7.5 fold. Each point in FIG. 1 and FIG. 12 represents the mean of duplicate determinations, and the results are representative of three experiments. Bovine thyroglobulin and bovine fetuin (obtained by ammonium sulfate fractionation of FCS, followed by gel filtration chromatography) were purchased from Sigma (St. Louis, Mo.), BSA (fraction V) from Boehringer Mannheim (Laval, Quebec), and TGF-β1 (purified human) from Collaborative Research (Bedford, Mass.). Before use, bovine thyroglobulin was spun twice in a centricon (M.W. cutoff of 10,000 Da) micro-concentrator (Amicon, Beverly, Mass.) to remove any excess Iodine and T3/T4 thyroid hormones.

FIG. 1 shows that bovine fetuin and bovine thyroglobulin neutralize the antiproliferative activity of TGF-β1 on cultures of Mv1Lu cells, a mink lung epithelial line which is highly sensitive to the anti-proliferative action of TGF-β1. Maximal effect for both fetuin and thyroglobulin was approximately 150% neutralization, suggesting that endogenous TGF-β in the cultures is also inhibited resulting in a net stimulation of cell growth compared to controls. Similar observations have been reported for the TGF-β antagonist decorin (Y. Yamaguchi, D. H. Mann, E. Ruoslahti, Nature 346, 281 (1990). S. Scholtz-Cherry J. E. Murphy-Ullrich, J. Cell Biol. 122, 923 (1993); O'Conner-McCourt, L, M. Wakefield J. Biol. Chem. 262, 14090 (1987); and, J. Massague Curr. Biol. 1, 117 (1991)).

Fetuin was able to inhibit the anti-proliferative activity of TGF-β1 on Mv1Lu cells in a dose dependent manner, with half-maximal inhibition (IC$_{50}$) at $4.2 \times 10^{-6}$ M. Thyroglobulin also neutralized TGF-β1 activity in the Mv1Lu growth inhibition assay with an IC$_{50}$=$2.2 \times 10^{-7}$ M (FIG. 1). The IC$_{50}$ for inhibition of TGF-β1 activity by thyroglobulin was 20 fold lower than for fetuin, a difference that is also reflected in the K$_D$ values for association of TGF-β with these glycoproteins (Table 1).

As shown in FIG. 12, fetuin stimulated proliferation of Mv1Lu cells (IC$_{50}$=8 pM). Neutralizing antibody to TGF-β1 also stimulated cell proliferation, suggesting that Mv1Lu cells produce active TGF-β, and cytokine antagonists can stimulate cell growth in the same manner as fetuin. Furthermore, fetuin blocked the anti-proliferative activity of exogenously-added TGF-β1, with an IC$_{50}$ of approximately $3 \times 10^{-6}$ M. BMP-2 also inhibited Mv1Lu cell growth (IC$_{50}$= 20 nM), but at a much higher concentration than TGF-β1. Fetuin reversed the effect of BMP-2 with an IC$_{50}$ of $2-5 \times 10^{-6}$ M (FIG. 12).

Example 2

To determine whether the action of fetuin as an antagonist of TGF-β1 in tissue culture was due to direct binding of the two proteins, their interaction by surface plasmon resonance using BIAcore (Pharmacia Biosensor, Piscataway, N.J.) (M. Malmqvist, Nature 361, 186 (1993) and S. C. Schuster, R. V. Swanson, L. A. Alex, R. B. Bourret, M. I. Simon, Nature 365, 343 (1993)) was examined. In this system, a purified protein serving as the ligand is covalently coupled to a carboxymethylated dextran surface, and binding molecules (i.e. the analyte) are passed in a fluid phase across the surface. Binding of the analyte to ligand causes a change in reflected light which is directly proportional to mass bound, and is measured in arbitrary response units (R.U.). Analyte-ligand binding is observed as both increasing response with time during the injection of analyte, and the difference in the position of the baseline before and after injection.

More particularly, purified human TGF-β1 (Collaborative Research, Bedford, Mass.) and recombinant human BMP-2 (a gift of Genetics Institute, Cambridge, Mass.) were immobilized onto the carboxy-methylated dextran surface of the CM5 sensor chip as described in M. Malmqvist, Nature 361, 186 (1993) and S. C. Schuster, R. V. Swanson, L. A. Alex, R. B. Bourret, M. I. Simon, Nature 365, 343 (1993). 1000 R.U. equals approximately 1 ng/mm$^2$. The running buffer was 20 mM Hepes (pH 7.2), 150 mM NaCl and the flow rate for all sensorgrams was 3 μl/min.

Fetal bovine fetuin (Sigma, Mo) and adult human fetuin/ α2-HS glycoprotein (Calbiochem, Ca) were purified by the manufacturers using different protocols. Regeneration of the surface to remove bound analyte was done by injection of 10 μl of 20 mM NaOH. To cyclize TRH1 peptides, the material was reduced with 5 mM DTT then brought to a final concentration of 60 μM in 25 mM ammonium acetate (pH 8.5). After stirring in the dark for 30 min at 20° C. with 30 mM potassium ferricyanide, the peptide was mixed with AG3-X4A resin (BioRad), filtered, lyophilization and desalted on a 50×2.5 cm column of Biogel P2 (Pharmacia) developed in water, and further purified by reverse phase HPLC. Ion spray mass spectroscopy confirmed cyclization and lack of peptide cross-linking.

Figure 3:
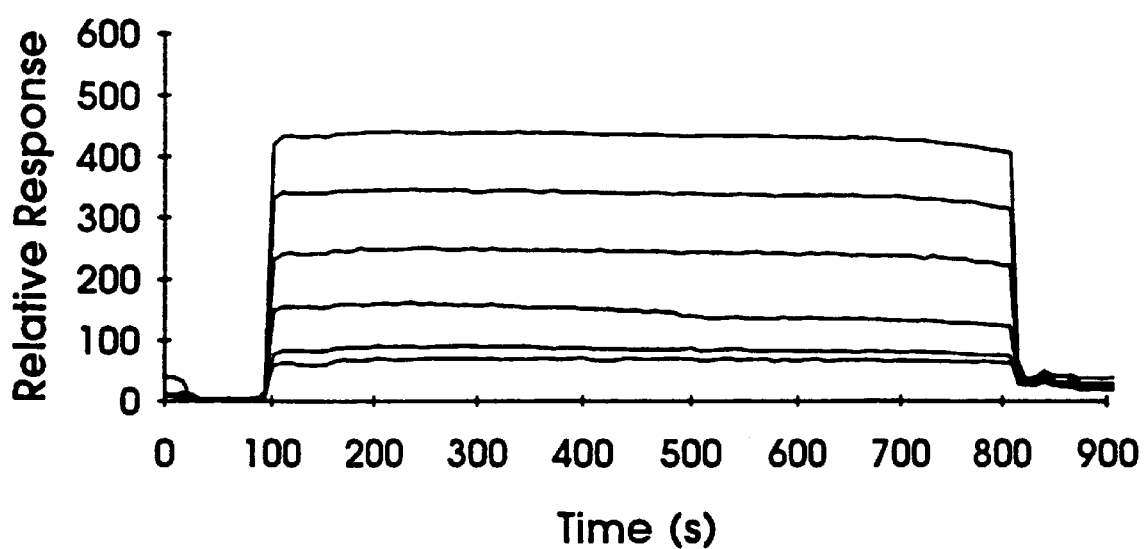
FIG. 3 is a sensorgram overlay plot of the non-binding control human transferrin.

Injection volumes were 36 μl for FIG. 2, 4 and 5 and 45 μl for FIG. 3. Regeneration of the surface to remove bound analyte was done by injecting 10 μl of 1M glucose-6-phosphate, or 1 μl of 20 mM NaOH for TGF-β1 and BMP-2 coated-surfaces, respectively. Protein concentrations in each experiment were (FIGS. 2 and 3), 2, 5, 10, 20, 30, 40 μM; (FIG. 4), 0.21, 0.31, 0.41, 0.62, 0.82, 1.24 μM; (FIG. 5), 0.22, 0.29, 0.44, 0.59, 0.88 μM. R.U. for the immobilized cytokine in each experiment was 2850 R.U. for FIGS. 2 and 3; 7450 R.U. for FIG. 4, and 5300 R.U., for FIG. 5 respectively.

Figure 4:
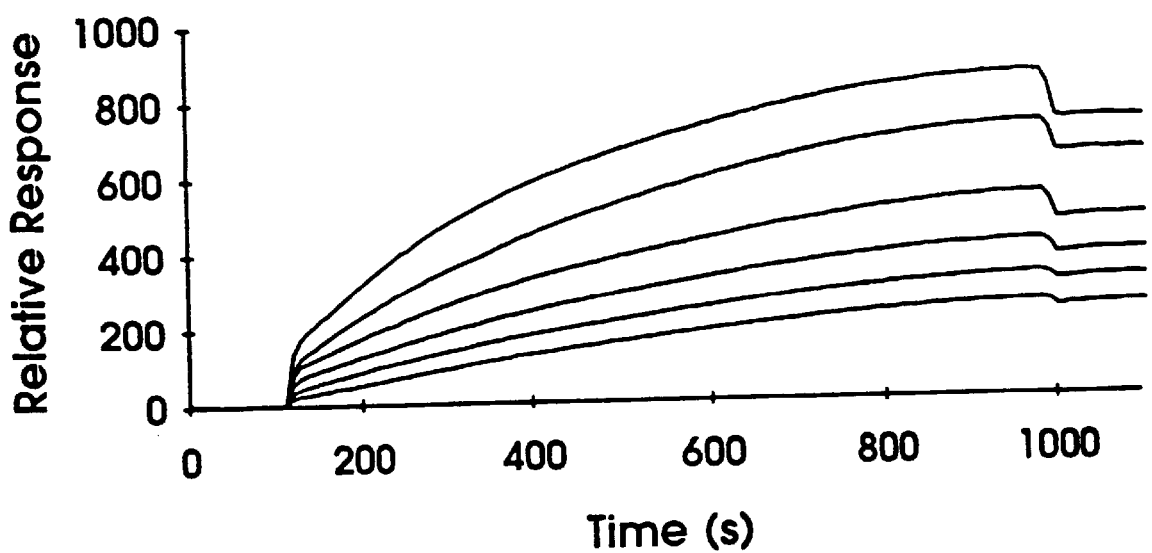
FIG. 4 is a sensorgram overlay plot showing bovine fetuin binding in response units (R.U.) to immobilized BMP-2.
Figure 5:
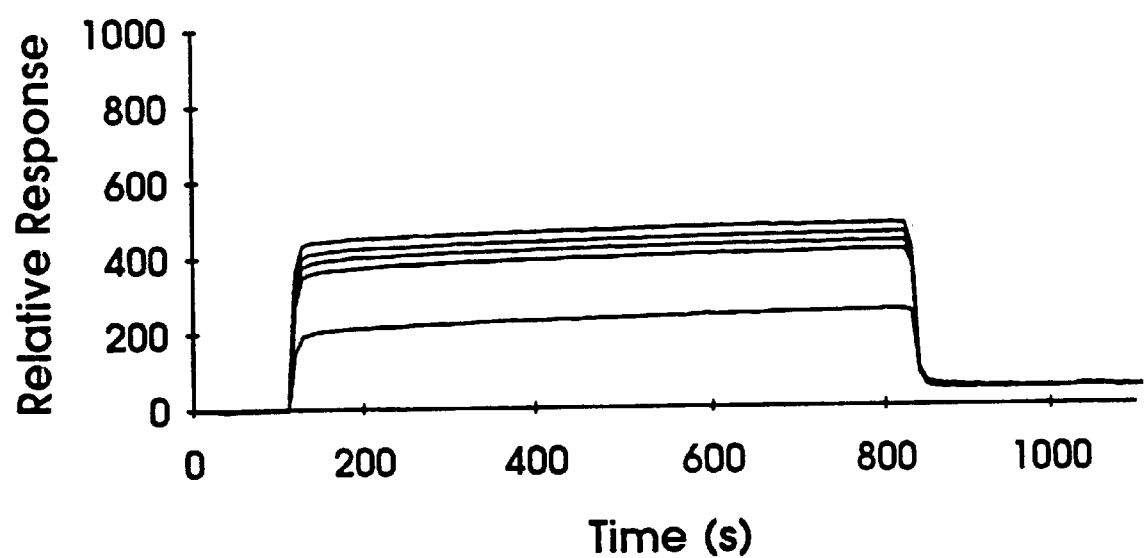
FIG. 5 is a sensorgram overlay plot of the non-binding control BSA.

The sensorgram overlay plots in FIGS. 2 to 5 show bovine fetuin binding in response units (R.U.) to immobilized TGF-β1 (FIG. 2); and to immobilized BMP-2 (FIG. 4). Each line from bottom to top represents increasing concentrations of injected analyte as detailed below. FIGS. 3 and 5 show the non-binding controls human transferrin passed over immobilized TGF-β1 and BSA passed over immobilized BMP-2, respectively. The large change in response at the beginning and end of injection is due to the change in refractive index caused by the protein in the injected buffer and does not indicate binding. Fetuin binding to TGF-β1 and BMP-2 is indicated by i) the increasing response with time during the injection, and ii) injection of increasing fetuin concentrations results in an incremental increase in response after the end of each injection. The fetuin-BMP-2 interaction shown in FIG. 4 does not come to equilibrium, whereas in FIG. 2 the lower affinity fetuin-TGF-β1 binding does come to equilibrium. Equilibrium is attained when the change in response with time is zero, as seen in panel (A) after approximately 200 seconds of fetuin binding to TGF-β1. Another control experiment showed that fetuin did not bind when a non-specific protein was immobilized (data not shown).

Binding constants for fetuin, thyroglobulin, and TRH1 peptides with TGF-β1 and BMPs were determined. Data was analyzed using the BIA-evaluation software (Pharmacia Biosensor). The association rate constant, $k_{ass}$, was calculated by first plotting the change in response with time versus response (i.e. dR/dT vs R). When the slope of the line from this graph is plotted versus analyte concentration (i.e d(dR/dT)/dR vs C), $k_{ass}$ is obtained from the slope of the line. The dissociation rate constant, $k_{diss}$, is obtained during the decrease in response with time after analyte injection is discontinued. Specifically, $k_{diss}$ was obtained from the slope of the line in a plot of $\ln(R_{t1}/R_{tn})$ vs time. The affinity constants were calculated from $K_D = k_{diss}/k_{ass}$. Variance for $k_{ass}$ is standard error of the linear regression plot, and for $k_{diss}$ values are the mean ± range of 3 or more independent injections. Steady state was observed for fetuin TGF-β1 binding, and analysis of these data by Scatchard plots produced a similar $K_D$ value, $4.6 \times 10^{-6}$ M. Tables 1 shows the binding constants for fetuin, thyroglobulin, TRH1b etc. interactions with cytokines. The calculations were repeated for fetuin and TRH1 binding to TGF-β cytokines, and the calculations are set out in Table 2. Bracketed numbers in Tables 1 and 2 are percent homology of the cytokines relative to BMP-2.

Analysis of the non-equilibrium binding data revealed an association rate (k.s.) for fetuin - TGF-β1 binding of 670 $M^{-1}s^{-1}$ and dissociation rates ($k_{diss}$) of $1.6 \times 10^{-1} s^{-1}$ (Table 1) and $1.9 \times 10^{-3}$ (Table 2). Using the data in FIG. 2, Scatchard type analysis for steady-state fetuin-TGF-β1 binding produced a $K_D$ value of $4.6 \times 10^{-6}$ M (data not shown), and the values 2.2 and $2.4 \times 10^{-6}$ M (Table 1 and Table 2, respectively) were obtained from $K_D = k_{diss}/k_{ass}$. This measure of fetuin-TGF-β1 affinity is similar to the $IC_{50}$ for fetuin neutralization of TGF-β1 activity (FIGS. 1 and 12), and is consistent with the view that fetuin neutralizes TGF-β1 activity by binding directly to the cytokine. Fetuin bound to the closely related cytokine TGF-β2, with similar affinity (Table 1 and Table 2).

Fetuin also bound to immobilized BMP-2 (FIG. 4), a TGF-β superfamily-member with 38% amino acid sequence identity to TGF-β1 (J. M. Wozney, V. Rosen, A. J. Celeste, L. M. Mitsock, M. J. Whitters, et al, Science 242, 1528 (1988) and V. Rosen, R. S. Thies, TIG 8, 97 (1992)). The affinity of fetuin binding to BMP-2 was approximately 100 times greater ($K_D = 3.6 \times 10^{-8}$ M, and $K_D = 2.7 \times 10^{-8}$ M, Table 1 and Table 2, respectively) than fetuin binding to TGF-β1. Both interactions showed a similar on-rate ($k_{ass} = 1.7 \times 10^3$ $M^{-1}s^{-1}$) but fetuin - BMP-2 had a much slower off-rate ($k_{diss}$32 $6.2 \times 10^{-5}$ $s^{-1}$ (Table 1) and $k_{diss} = 6.5 \times 10^{-5}$ (Table 2)), accounting for most of the difference in affinity. Fetuin also bound to immobilized BMP-4 and BMP-6 with characteristic affinities that differed largely due to changes in off-rates (Table 1 and Table 2). It is interesting to note that affinities for fetuin binding to the five cytokines showed a direct correlation with amino acid homology to BMP-2, the cytokine with the highest affinity for fetuin (Table 1 and Table 2). The rank order of $K_D$s measurements for fetuin-cytokine binding were BMP-2<BMP-4<BMP-6<TGF-β1<TGF-β2, which correlates with their primary sequence homology to BMP-2 (Table 1 and Table 2).

Thyroglobulin was also tested for binding to the BMPs and TGF-β in the BIAcore assay described above. Surprisingly, thyroglobulin bound with higher affinity than fetuin to the cytokines, showing the strongest interaction with BMP-2 ($K_D = 3.1 \times 10^{-9}$ M). Thyroglobulin bound to BMP-2 >BMP-4>TGF-β1>TGF-β2, a rank order similar to that observed for fetuin binding to these cytokines (Table 1 and Table 2). Thyroglobulin is found at low levels in serum, and at much higher concentrations in the follicles of the thyroid where it is a precursor to thyroxine. TGF-β has been shown to inhibit thyroglobulin biosynthesis and thyroid cell proliferation in vitro (Colletta et al. Cancer Res. 49, 3457, 1989). In this context, the results of the present studies suggest that thyroglobulin may bind to and antagonize this action of TGF-β in the thyroid.

Example 3

The amino acid sequences of fetuin and TGF-β receptor type I or type II were compared to identify a cytokine-binding domain. The fetuin and TβRII sequences were first aligned by positioning of the cysteine residues. The TGF-β type I (Tsk 7L) receptor shown in FIG. 8 is aligned with TβRII as in H. Y. Lin, X. -F. Wang, E. Ng-Eaton, R. A. Weinberg, H. F. Lodish, Cell 68, 775 (1992). The TGF-β type I (Tsk 7L) receptor shown in FIG. 8 is aligned with TβRII as in Ebner et al. Science 260, 1344–1348, 1993. Visual examination of the alignment revealed the 43 amino acid homology domain designated TGF-β Receptor II Homology 1 domain (TRH1) (FIG. 8). The TRH1 domain is present in TβRII, ActRII and ActRIIb, but absent in the type I receptors (Lin et al., Cell 68, 775–785, 1992; Ebner et al., Science 260, 1344–1348, 1993; Attisano et al., Cell 75, 671–680, 1993; Franzen et al., Cell 75, 681–692, 1993; Bassing et al., Science 263, 87–89, 1994) which do not bind cytokines in the absence of type II receptors (Wrana et al., Cell 71, 1003–1014, 1992; Wrana et al., Nature 370, 341–347 1994). The intramolecular disulfide bonds of human fetuin have previously been determined (J. Kellermann, H. Haupt, E. -A. Auerswald, W. Müller-Esterl, J. Biol. Chem 264, 14121 (1989). The TRH1 domain in fetuin forms a peptide loop in the amino end structural duplication. The structural duplications are indicated as the larger semi-circles in FIG. 7, and are designated a and b (FIGS. 7 and 8).

Figure 7:
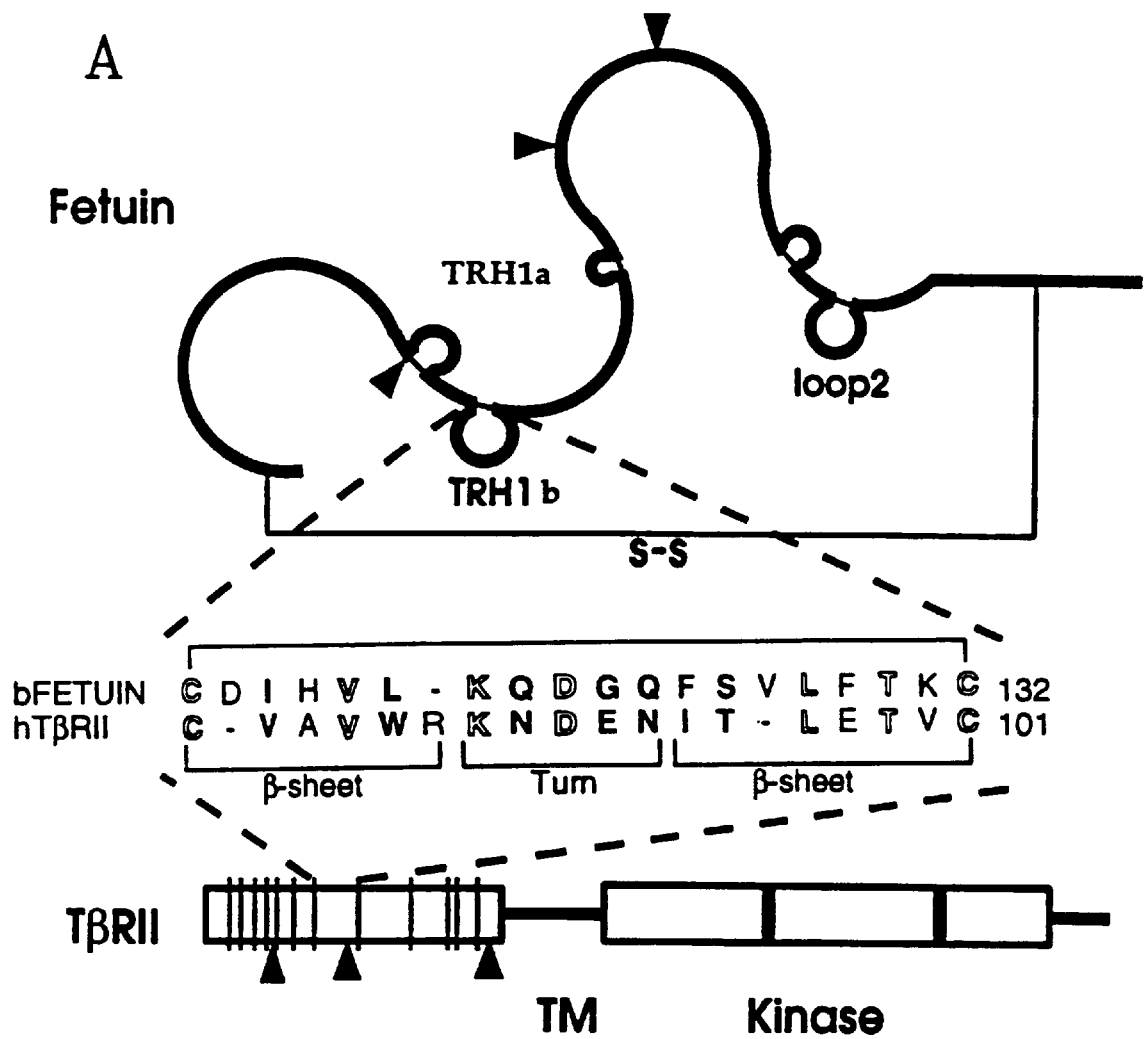
FIG. 7 is a schematic drawing of the disulfide loop structure of fetuin.

As shown in FIG. 7, each structural duplication in fetuin contains two disulphide loops, including the TRH1 domain (position 114–132), and the inactive loop2 (i.e. position 230–248). TM and kinase indicate transmembrane domain and protein-kinase domains of TβRII, respectively. The Chou-Fasman (Chou and Fasman, 1978) and Garnier, Osguthorpe, and Robson (Garnier et al., 1978) methods of predicting secondary structure produced similar results for the TRH1 domain of fetuin and TβRII as indicated below the sequences in FIG. 7.

Figure 13:
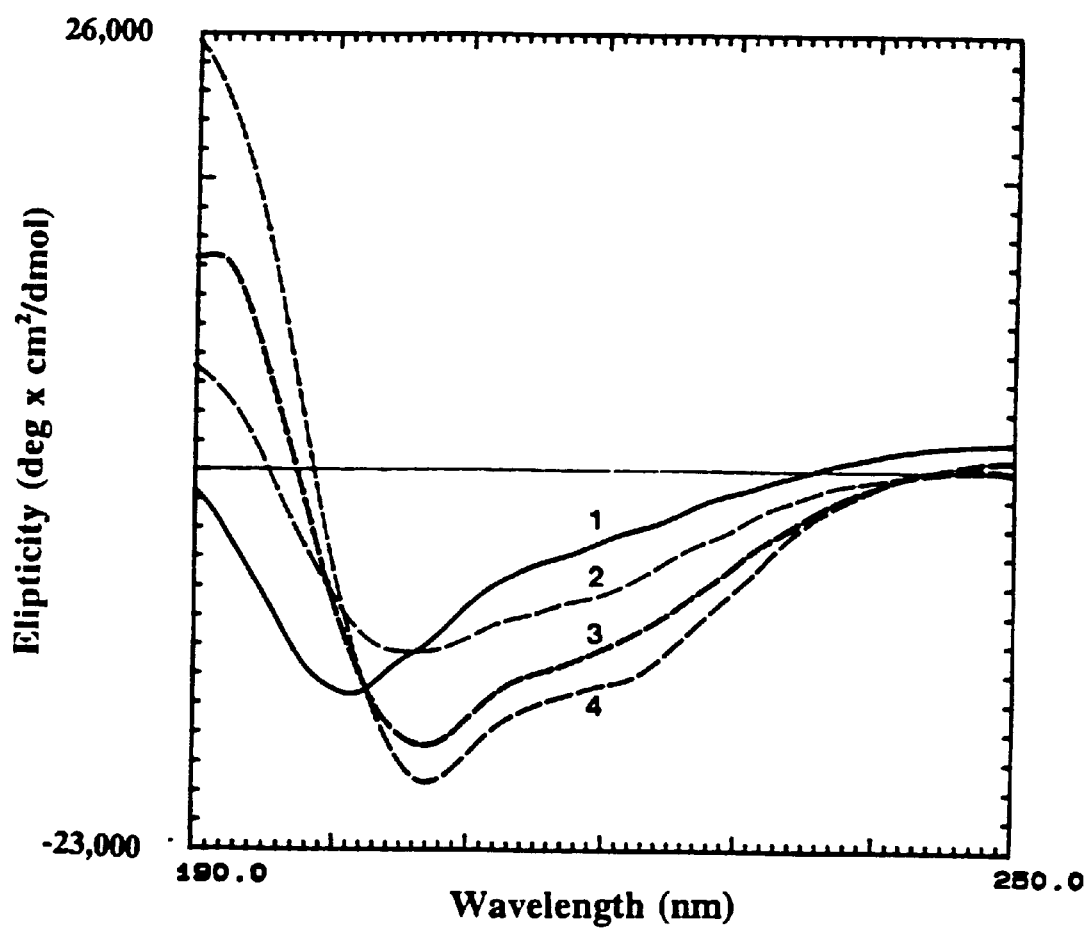
FIG. 13 is a low-ultraviolet CD spectra of 18 amino acid cyclized TRH1 peptides.

Algorithms for secondary-structure predict a β-sheet-turn-β-sheet arrangement for the TRH1 peptides of fetuin, TβRII and the type II activin receptors, but this structure is not predicted for loop2, the analogously-positioned loop in the carboxy end of fetuin (FIG. 7). Low-ultraviolet CD spectra of the cyclized TRH1 peptides preformed indicates the presence of 58% β-sheet, 41% random coil consistant with the prediction algorithm (FIG. 13).

The TRH1 domain and flanking sequences in fetuin are highly conserved across species (i.e. human, bovine, sheep, rat, mouse)(Dziegielewska et al., J. Biol. Chem. 265, 4354–4357 1990; Rauth et al., J. Biochem. 204, 523–529, 1992; lee et al., Proc. Natl. Acad. Sci. U.S.A. 84, 4403–4407 1987; Brown et al., Eur. J. Biochem. 321–331 1992), relative to the carboxy half of the molecule (See FIG. 6). Indeed, human fetuin (α2-HS glycoprotein) bound to BMP-2 with similar affinity as that of bovine fetuin (data not shown).

A search of the PIR protein sequence data bank for other proteins containing the TRH1 domain was conducted using the GCG routine "findpatterns" and the following pattern: CX{8,14} (N,Q)X{12,16}CX{4,5} (K,R) X {2,6} (S,T)

X{4,9} CX{0,2}DX{5,6}(D,E). The pattern was based on conserved amino acids between fetuin, TβRII, daf-1, and activin receptor type II. The search yielded 46 matches, most of which were extracellular domains of receptors or secreted glycoproteins and included, fetuins (n=5), kinnogens which are distant family members of the fetuins (J. Kellermann, H. Haupt, E. -A. Auerswald, W. Müller-Esterl, J. Biol. Chem 264, 14121 (1989)) (n=5), daf-1 (n=1), activin receptor type II (n=5), bovine thyroglobulin (L. Mercken, M. -J. Simons, S. Swillons, M. Hassaer, G. Vassart, Nature 316, 647 (1985)) (n=1), EGF receptor (n=2), LDL receptor (n=1), IL-1 receptor (n=1) and drosophila crumbs (n=1). The number in brackets indicates the number of matches; for example fetuin from 5 species.

A low stringency search of the PIR protein data bank was also done using conserved residues in the TRH1 domains of fetuin and the type II receptors for TGF-β and activin was performed. The GCG routine "findpatterns" and the following pattern were used: CX{0,1}(V,I,F,Y)X{1,3} (V,W,L) X{0,1}(K,R)X{4,5} (V,I,F)X{1,2} (L,I)X{2,4}CX{0,2}D. The search yielded 32 matches, 25 of which represented fetuin (n=5), TβRII (n=2), and type II activin receptors (n=18) from various species.

Similarity in sequence between the TRH1b subdomains of TβRII, fetuin and thyroglobulin was striking, ranging from 63% to 71% (FIG. 8). Therefore, thyroglobulin was tested for binding to the BMPs and TGF-β in the BIAcore assay as described in Examples 1 and 2.

Example 4

The TGF-β and activin type I receptors lack the TRH1b sequence (FIG. 8), and do not bind ligand in the absence of type II receptors (R. Ebner, R. -H. Chen, L. Shum, S. Lawler, T. F. Zioncheck, et al, Science 260, 1344 (1993); L. Attisano, J. Carcamo, F. Ventura, F. M. B. Weis, J. Massague, et al, Cell 75, 671 (1993); P. Franzen, P. ten Dijke, H. Ichijo, H. Yamashita, P. Schulz, et al, Cell 75, 681 (1993); C. H. Bassing, J. M. Yingling, D. J. Howe, T. Wang, W. W. He, et al, Science 263, 87 (1994); and J. L. Wrana, L. Attisano, J. Carcamo, A. Zentella, J. Doody, et al, Cell 71, 1003 (1992)). This suggested that the TRH1b subdomain of type II receptors may be directly involved in cytokine binding. To examine this possibility, TRH1b peptides from both fetuin and TβRII were synthesized and a cyclized TRH1b peptide was prepared. The TRH1 peptides and cyclized peptide were tested for binding to TGF-β1 and BMP-2.

The cyclized TRH1b peptide was prepared by first reducing the peptide with DTT to remove dimers, trimers etc. and then bringing to a final concentration of 60 μM in 25 mM ammonium acetate (pH 8.5). After stirring in the dark for 30 min at 20° C. with 30 mM potassium ferricyanide, the peptide was mixed with AG3-X4A resin (BioRad) and filtered. Following lyopholization, the sample was desalted on a 50×2.5 cm column of Biogel P2 (BioRad) developed in water. Ion spray mass spectroscopy confirmed cyclization and did not detect the presence of multimers. Peptide, in 0.15M Tris pH 8.0, 0.15M NaCl, 2 mM EDTA, was reduced and alkylated by first boiling in 90 fold excess DTT for 10 min., followed by a 15 min incubation with 45 fold excess iodoacetamide (Pierce) in the dark with shaking. The sample was desalted on a P2 column. Ion spray mass spectroscopy confirmed reduction and alkylation of the peptide.

Figure 9:
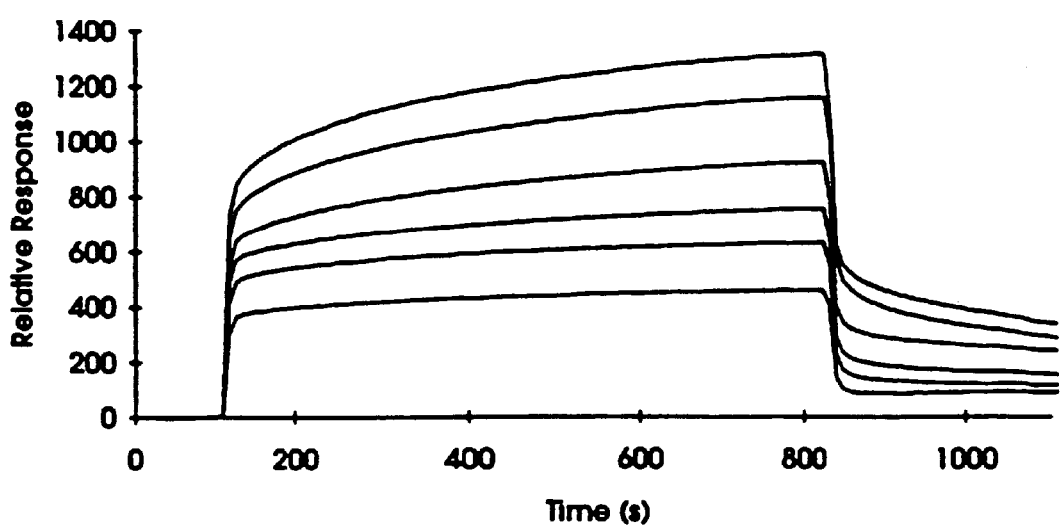
FIG. 9 is a sensorgram plot showing the binding of the disulfide-looped TRH1b fetuin peptide to immobilized BMP-2.
Figure 10:
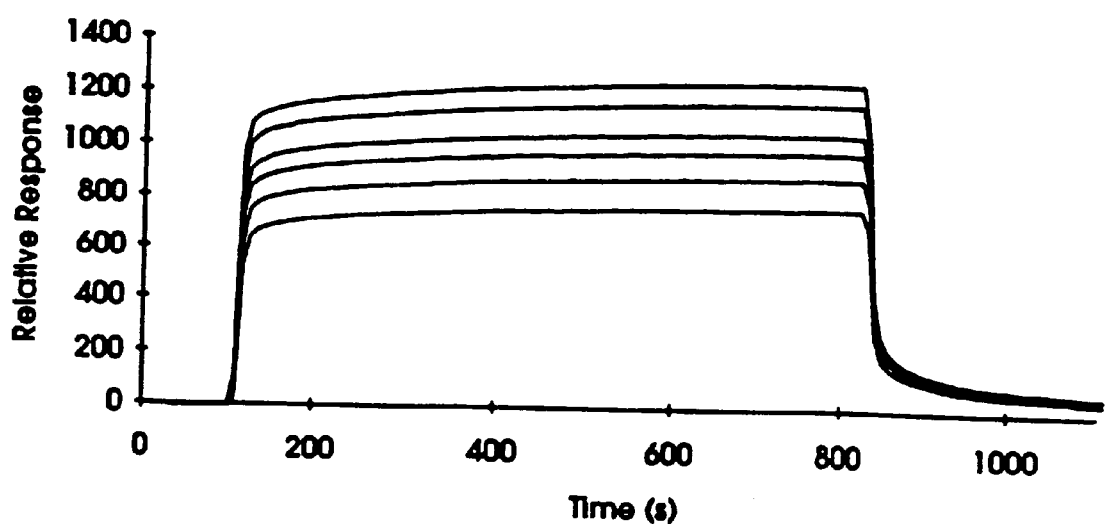
FIG. 10 is a sensorgram plot showing the lack of binding of reduced and alkylated TRH1b peptide.

FIG. 9 is a sensorgram overlay plot displaying binding of the disulfide-looped TRH1b fetuin peptide to immobilized BMP-2 (5300 R.U. immobilized) at 6 concentrations (87, 130, 174, 217, 283, and 348 μM). FIG. 10 is a sensorgram plot showing the lack of binding of reduced and alkylated THR1b peptide at the same concentrations. As the BIAcore signal measures mass, the lower molecular weight TRH1b peptide made it necessary to use near-saturating binding conditions to observe signal. Saturation was determined to be approximately 550 R.U. Competition of fetuin- BMP-2 binding by cyclized TRH1b peptide was observed, and to a much lesser extent, by the reduced and alkylated peptide (data not shown). Since TRH1b peptide is 1/20 the mass of fetuin, and therefore gives proportionally less signal per molecule bound, a reduction in response was observed when low concentrations of TRH1b were co-injected with fetuin, compared to fetuin alone. However, it was not possible to separate in a quantitative manner, the fetuin and THR1b peptide BIAcore signals observed with the non-equilibrium conditions experienced in these experiments.

The results demonstrate that the intramolecular disulfide-looped form of the fetuin TRH1b peptide bound directly to immobilized BMP-2 with a $K_D$=3.2×10$^6$ M (FIG. 9, Table 1) and a $K_D$=2.4×10$^6$ M (Table 2), and also competed for fetuin-BMP-2 binding in a dose dependent manner. However, no significant binding to BEP-2 was observed when this peptide was reduced and alkylated (FIG. 9). This is consistent with the observation that reduced and alkylated fetuin had diminished binding to BMP-2 and TGF-β1 compared to native fetuin (data not shown). This suggests that disulphide-looping stabilizes a preferred TRH1 peptide structure for cytokine binding. The on-rate for disulfide-looped TRH1b peptide binding to BMP-2 is similar to that for intact fetuin, whereas the off-rate of TRH1b is 100 times faster (Table 1 and Table 2). This suggests that the TRH1b domain in fetuin is the major peptide motif involved in the initial recognition and binding to cytokine. Other portions of the fetuin protein may stabilize binding and/or-the conformation of the TRH1b peptide loop, thereby slowing fetuin's off-rate when compared with the peptide.

If cytokine binding to TβRII is mediated by the TRH1b sequence, the known cytokine specificity of the receptors (J. L. Wrana, L. Attisano, J. Carcamo, A. Zentella, J. Doody, et al, Cell 71, 1003 (1992)) predicts that the peptide sequence from TβRII should bind to TGF-β1 with higher affinity then to BMP-2. BIAcore binding data confirmed this prediction (See Example 5 and Table 1, and Table 2). The cyclized TβRII peptide bound to TGF-β1 with higher affinity than to BMP-2 (i.e. $K_D$5.2×10$^{-7}$ M and >10$^{-5}$, respectively), a reversal of binding preference shown by the TRH1b peptide from fetuin (Table 1 and Table 2). This suggests that the TRH1b sequences can dictate ligand binding affinities and therefore ligand specificity.

Example 5

Competition of TGF-β1 binding to immobilized TβRII using fetuin and looped TRH1 peptide from TβRII.

Figure 14:
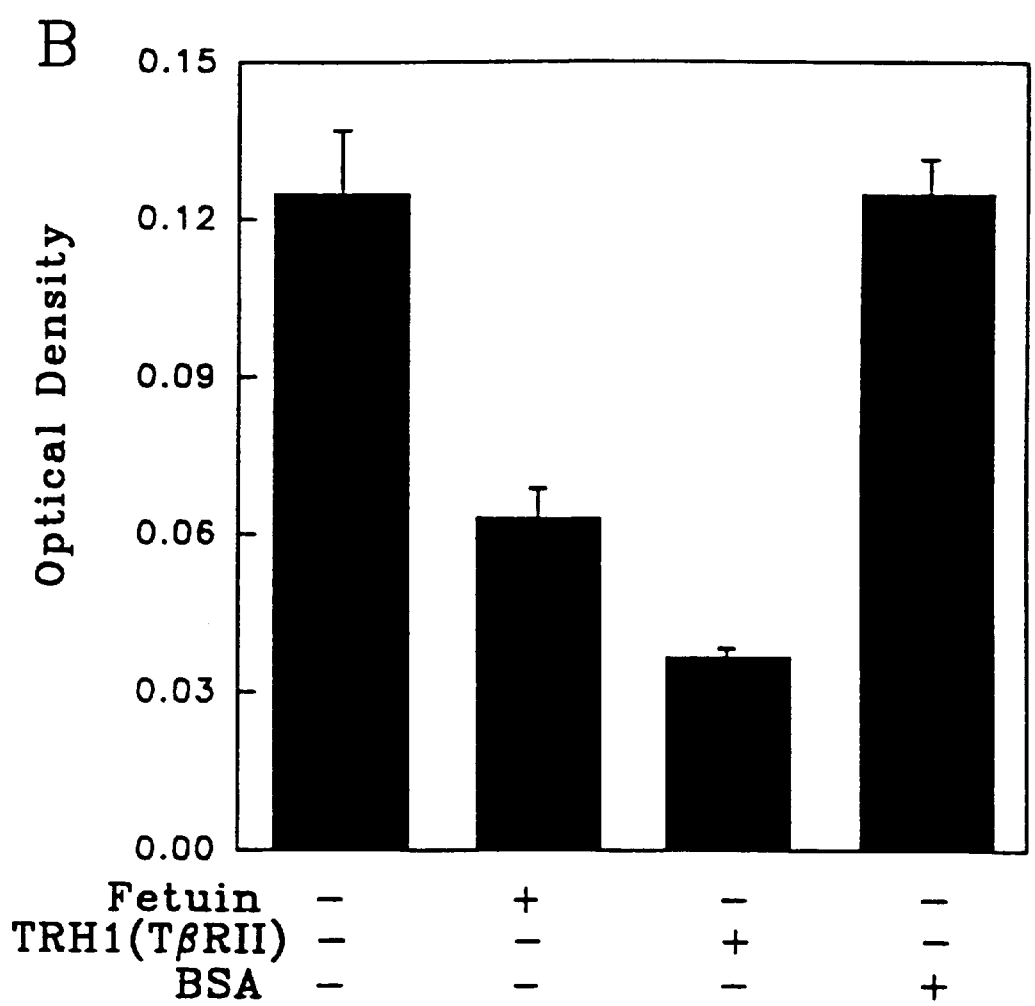
FIG. 14 is a bar graph showing competition of TGF-β1 binding to immobilized TRH1 using fetuin and looped TRH1b peptides from TRH1.

Inhibition of TGF-β1 binding to TβRII was carried out using the Quantikine ELISA kit (R&D Systems). In particular, 96 well plates were pre-coated with the extracellular domain of TβRII. To study competition of TGF-β1 binding, the cytokine was brought to a final concentration of 40 pM in diluent provided with the kit, either alone or with antagonists fetuin (40 μM), TRH1 peptide from TβRII (20 μM) or BSA (40 μE) for 1.5 hr at 20° C. in siliconized Eppendorf tubes with shaking. This was followed by a 5 minute incubation with the TβRII coated ELISA wells with shaking, washing as recommended, and a 1 hr incubation with the polyclonal anti-TGF-β1 antibody. Plates were developed as per the instructions, and determinations were made in triplicate. FIG. 14 shows that the TRH1b peptide and fetuin serve as competitive inhibitors of TGF-β1 binding to immobilized recombinant TβRII. Therefore, TRH1b appears to be the primary recognition site in TβRII, and sequence differences amongst the TRH1b domains of type II receptors and fetuin may largely dictate cytokine specificity.

The experiments described in the above Examples define a disulfide-looped motif common to TβRII, fetuin and thyroglobulin which mediates binding to two divergent members of the TGF-β superfamily. The TRH1 motif is conserved in the ligand-binding TβRII family members including activin type II[18] and daf-1 receptors, but is absent in the TGF-β/activin type I receptors; the latter are unable to bind cytokine in the absence of type II receptors. Fetuin and thyroglobulin have significantly higher affinities for BMP-2 than for TGF-β1 suggesting that variations in both TGF-βs and TRH1 sequences may dictate ligand -receptor/antagonist specificity through changes in binding-affinity. The results also suggest a hitherto unknown function for fetuin and thyroglobulin as antagonists of TGF-β superfamily members in vivo and may explain the mechanism for the broad biological activities ascribed to fetuin.

Example 6

Figure 16:
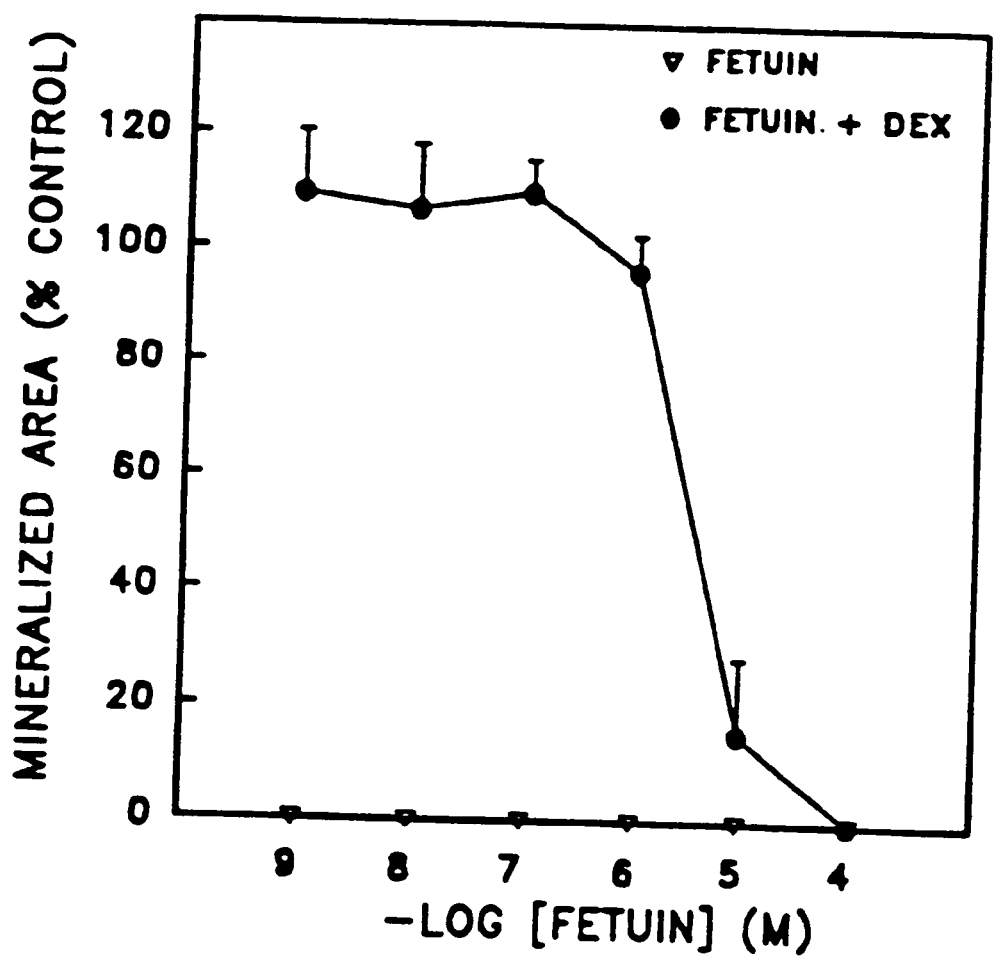
FIG. 16 is a graph showing that fetuin inhibits subsequent mineralization in the dexamethasone-treated cultures when present from 1 through 3 weeks; and lacks osteogenic activity alone.
Figure 17:
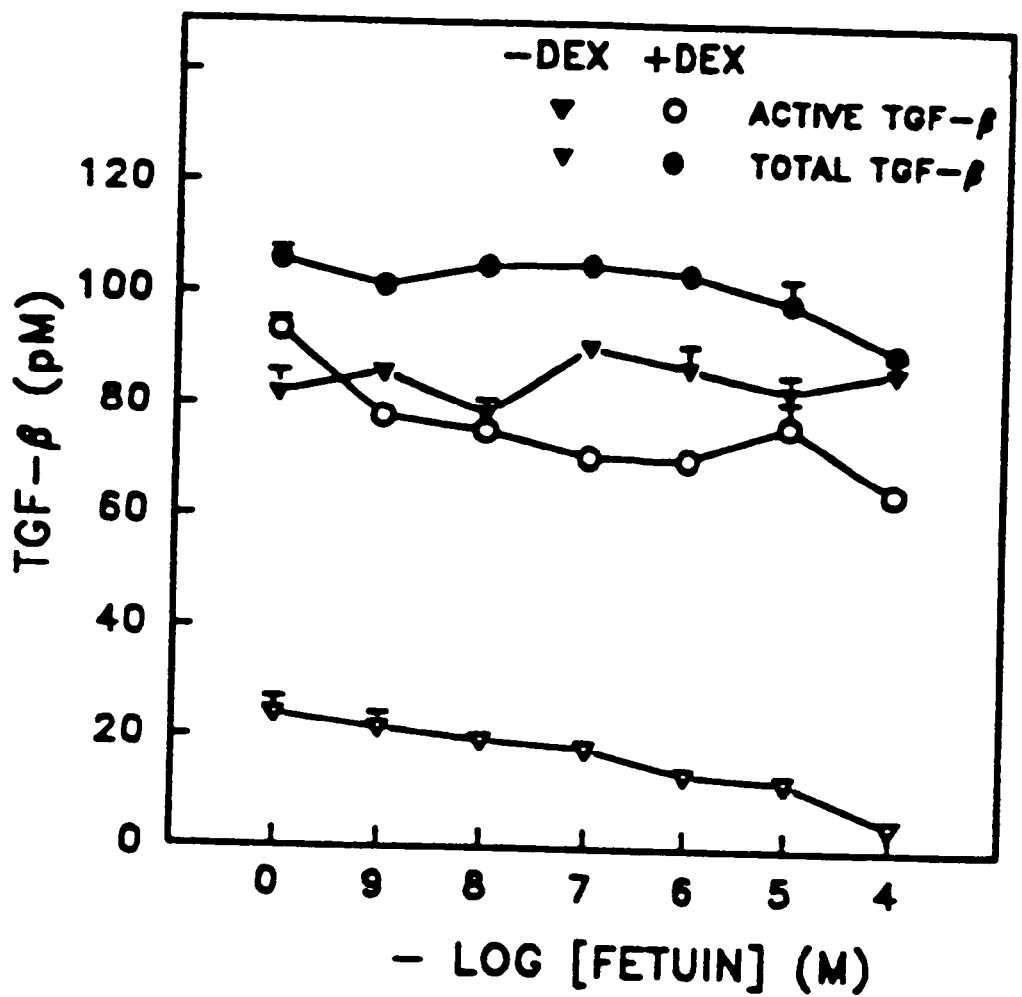
FIG. 17 is a graph showing active TGF-β, and total TGF-β measured in dexamethasone-treated and untreated cultures.

The methods used in the studies described in this example and illustrated in FIGS. 16 and 17 are as follows. Femoral bones were removed under aseptic conditions from adult male Wistar rats (120 g), cleaned of adherent soft tissues, and washed extensively in antibiotics. The distal ends were removed and the marrow contents were flushed out with 10 ml of culture medium. The cells were dispersed by repeated passage through a 20 gauge needle and incubated in alpha-MEM supplemented with 15% fetal bovine serum, ascorbic acid (50 μg/ml), antibiotics (penicillin G 100 μg/ml, gentamicin 50 μg/ml, fungizone 0.3 μg/ml) and 10 mM β-glycerophosphate. The culture media were supplemented further with dexamethasone alone ($10^{-8}$M), or with the various concentrations of fetuin. Following 6 days of culture at 37° C. in a humidified atmosphere containing 5% $CO_2$ in air, the cells were re-plated at a density of $1 \times 10^2$ cell/mm$^2$ in 96 multi-well plates (Falcon 3047), and grown for another 12–14 days. At the end of culture, the cells were fixed and stained for calcium with alizarin red-s for quantification of bone nodule area (reported as mineralized area (mm$^2$)/well). To assess mineralized tissue formation in the cultures morphometric measurements were carried out with the aid of a Bioquant IV system (Bioquant, Nashville, Tenn., U.S.A.) using a Leitz Orthoplan microscope. TGF-β in culture supernatants taken 4 days prior to scoring mineralization were measured with and without heat activation (80° C. for 10 min) using the Mink cells as the indicator cell line as described in FIG. 12. Neutralizing anti-TGF-β antibodies supplied by R&D systems were specific for TGF-β1 and with 100 fold lower reactivity for TGF-β2 and β3.

Figure 15:
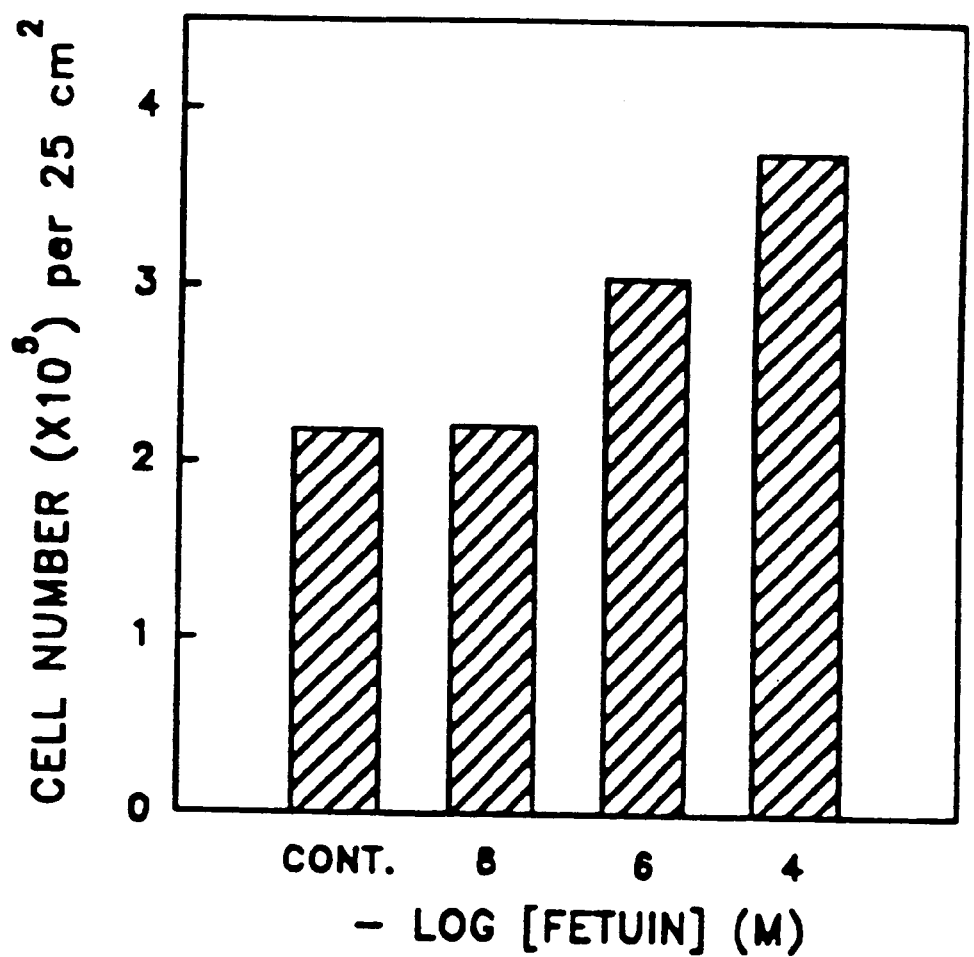
FIG. 15 is a graph showing that fetuin stimulates proliferation of rat bone-marrow cells treated with dexamethasone for 6 days.
Figure 18:
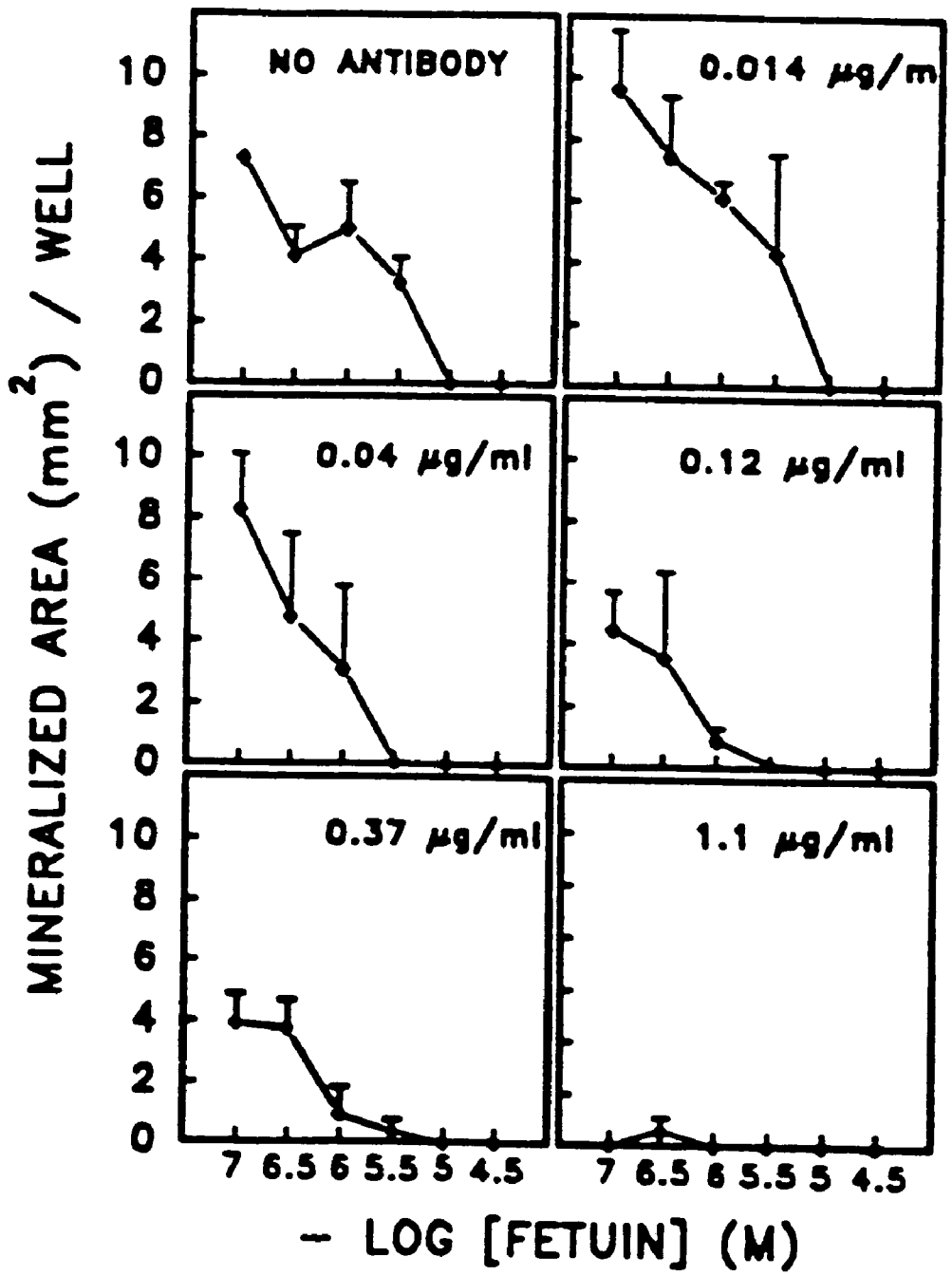
FIG. 18 are graphs showing that neutralizing anti-TGF-β antibodies suppressed mineralization and were additive with fetuin in the 1–3 week culture period.

With fetuin's greater affinity for BMPs, as well as co-localization of fetuin and BMPs in developing bone (Rosen and Thies, Trends Genet. 8, 97–102, 1992; Wozney et al., Science 242, 1528–1534, 1988), fetuin-cytokine interactions may play a role in bone cell differentation. To examine this possibility, rat bone marrow stromal cells were cultured in the presence of dexamethasone which induces osteogenic differentiation with deposition of calcium-containing matrix after three weeks of culture (FIGS. 15 to 18). The addition of exogenous TGF-β at an early stage of culture inhibits cell proliferation (Oursler et al., Endocrinology 133, 2187–2196 1993), but in the latter phase of osteogenic differentiation, the cytokine is necessary for deposition of matrix (Van Vlasselaer et al., J. Cell Biol. 4, 569–577, 1994). During the first week of culture, which is the proliferative phase, the addition of fetuin stimulated an increase in cell number, consistent with its role as a TGF-β antagonist (FIG. 15). When added during the latter two weeks of culture, fetuin inhibited deposition of calcium-containing matrix, also as expected of a TGF-β antagonist (FIG. 16). The $IC_{50}$ for inhibition of calcium-deposition was approximately $10^{-5}$M, a concentration only 5 fold greater than the BIAcore measurement of $K_D$ for fetuin-TGF-β binding. Since fetuin is present in the 15% FCS of the culture medium at concentrations of $2–3 \times 10^5$, this represents only a 30–50% increase in fetuin concentrations. Dexamethasone increased TGF-β levels in the rat bone marrow cultures by inducing activation of latent cytokine (FIG. 17). Although total cytokine levels remained similar, the fraction of active TGF-β increased 3 fold in dexamethasone-treated cultures. Data in FIG. 18 shows that neutralizing anti-TGF-β antibodies alone, or in combination with fetuin completely block deposition of calcium-containing matrix in the dexamethasone-treated bone marrow cultures. This confirms the requirement for TGF-β to complete the final stages of differentiation, but does not exclude the involvement of other TGF-β family members. The suppressive effect of fetuin on deposition of calcium-containing matrix is not likely due to cytotoxicity, as marrow cell proliferation as stimulated by fetuin during the first week of culture (FIG. 16). BMP-2 also induced osteogenesis in these cultures which could be blocked by the addition of fetuin (data not shown).

In summary, the above experiments define a disulphide-looped motif present in TβRII and fetuin which mediates binding to multiple members of the TGF-β superfamily. The TRH1 motif is also found in the activin type II receptors (Mathews and Vale, 1991), but is absent in type I cytokine receptors (Ebner et al., 1993; Attisano et al., 1993; Franzen et al., 1993; Wrana et al., 1992). The results also indicate a hitherto unknown function for fetuin as an antagonist of TGF-β superfamily members in vivo, and may explain the mechanism for the various biological activities previously ascribed to fetuin (Nie, Am. J. Med., 1994). Most notably, fetuin via the circulation accumulates in bone (Dickson et al., Nature 256, 430–432 1975; Triffitt et al., Nature 262, 226–227, 1976), with highest concentrations found at locations of bone growth, where it may regulate the bone promoting activity of BMPs (Wozney et al., Science 242, 1528–1534, 1988; Rosen and Thies, 1992) and TGF-βs (Massagué, 1990). In Paget's disease an affliction of increased bone turnover with disordered and thickened bone, serum fetuin levels are depressed, whereas fetuin is elevated in a subset of osteogenesis imperfecta patients. Finally, cytokine antagonists based on the TRH1b peptide would appear to be useful in the treatment of immune suppression in cancer patients and fibrotic disorders (Massagué, 1990), such as glomerulonephritis (Border et al., Nature 360, 361–364, 1992) and atherosclerosis (Ross, Nature 362, 801–809, 1993) where elevated cytokine activity are known to play a role (Border and Ruoslahti, J. Clin. Invest. 90, 1–7, 1992).

The present invention has been described in detail and with particular reference to the preferred embodiments; however, it will be understood by one having ordinary skill in the art that changes can be made thereto without departing from the spirit and scope thereof.

All publications, patents and patent applications referred to herein, are herein incorporated by reference in their entirety to the same extent as if each individual publication, patent or patent application was specifically and individually indicated to be incorporated by reference in its entirety.

Forming part of the present disclosure are the appended sequence listings.

TABLE 1

Binding constants for fetuin, thyroglobulin and TRH1b interactions with cytokines

| Analyte | Ligand | $k_{ass}$ (M$^{-1}$s$^{-1}$) | $k_{diss}$ (s$^{-1}$) | $K_D$ (M) |
|---|---|---|---|---|
| Fetuin | TGF-β1 (38%) | $6.7 \times 10^2 \pm 4.0 \times 10^2$ | $1.6 \times 10^{-3} \pm 0.4 \times 10^{-3}$ | $2.4 \times 10^{-6}$ |
|  | TGF-β2 (36%) | $5.5 \times 10^2 \pm 1.2 \times 10^2$ | $3.2 \times 10^{-3} \pm 0.5 \times 10^{-3}$ | $5.8 \times 10^{-4}$ |
|  | BMP-2 (100%) | $1.7 \times 10^3 \pm 0.3 \times 10^3$ | $6.2 \times 10^{-5} \pm 3.6 \times 10^{-5}$ | $3.6 \times 10^{-8}$ |
|  | BMP-4 (86%) | $4.2 \times 10^3 \pm 0.2 \times 10^3$ | $5.8 \times 10^{-4} \pm 0.1 \times 10^{-4}$ | $1.4 \times 10^{-7}$ |
|  | BMP-6 (57%) | $2.9 \times 10^3 \pm 0.5 \times 10^3$ | $2.5 \times 10^{-3} \pm 0.5 \times 10^{-3}$ | $8.6 \times 10^{-7}$ |
| Thyroglobulin | TGF-β1 | $2.8 \times 10^3 \pm 1.0 \times 10^3$ | $1.9 \times 10^{-3} \pm 0.8 \times 10^{-3}$ | $6.8 \times 10^{-7}$ |
|  | TGF-β2 | $1.3 \times 10^3 \pm 0.6 \times 10^3$ | $5.0 \times 10^{-3} \pm 0.5 \times 10^{-3}$ | $3.8 \times 10^{-6}$ |
|  | BMP-2 | $3.2 \times 10^4 \pm 0.2 \times 10^4$ | $1.0 \times 10^{-4} \pm 0.1 \times 10^{-4}$ | $3.1 \times 10^{-9}$ |
|  | BMP-4 | $5.4 \times 10^4 \pm 0.7 \times 10^4$ | $1.1 \times 10^{-3} \pm 0.4 \times 10^{-3}$ | $2.0 \times 10^{-8}$ |
| TRH1b (fetuin) | BMP-2 | $1.6 \times 10^3 \pm 0.5 \times 10^3$ | $5.1 \times 10^{-3} \pm 1.1 \times 10^{-3}$ | $3.2 \times 10^{-4}$ |
|  | TGF-β1 | — | — | $>10^{-5}$ |
| (reduced & alkylated) | BMP-2 | — | — | $>10^{-5}$ |
| TRH1b (TβRII) | BMP-2 | — | — | $>10^{-5}$ |
|  | TGF-β1 | $3.7 \times 10^3 \pm 2.9 \times 10^3$ | $1.9 \times 10^{-3} \pm 0.5 \times 10^{-3}$ | $5.2 \times 10^{-7}$ |
| (reduced & alkylated) | TGFβ1 | — | — | $>10^{-5}$ |

Binding constants for fetuin, thyroglobulin and TRH1b peptides with TGF-β and BMPs. Data was analyzed using the BIA-evaluation software (Pharmacia Biosensor). The association rate constant, $k_{ass}$, was calculated by first plotting the change in response with time versus response (ie. dR/dT vs R). When the slope of the line from this graph is plotted versus analyte concentration (i.e d(dR/dT)/dR vs C). $k_{ass}$ is obtained from the slope of the line. The dissociation rate constant, $k_{diss}$, is obtained during the decrease in response with time after analyte injection is discontinued. Specifically, $k_{diss}$ was obtained from the slope of the line in a plot of $\ln(R_{tl}/R_{tn})$ vs time. The affinity constants were calculated from $K_D = k_{diss}/k_{ass}$. Variance for $k_{ass}$ is standard error of the linear regression plot, and for $k_{diss}$ values are the mean ± range of 3 or more independent injections. Bracketed numbers are percent homology of the cytokines relative to BMP-2.

TABLE 2

Fetuin and TRH1 binding to TGF-β cytokines

| Analyte | Ligand | $k_{ass}$ (M$^{-1}$s$^{-1}$) | $k_{diss}$ (s$^{-1}$) | $K_D$ (M) |
|---|---|---|---|---|
| b-Fetuin | TGF-β1 (38%) | $8.7 \times 10^2 \pm 2.7 \times 10^2$ | $1.9 \times 10^{-3} \pm 0.6 \times 10^{-3}$ | $2.2 \times 10^{-6}$ |
|  | TGF-β2 (36%) | $5.5 \times 10^2 \pm 1.2 \times 10^2$ | $2.4 \times 10^{-3} \pm 0.3 \times 10^{-3}$ | $4.4 \times 10^{-6}$ |
|  | BMP-2 (100%) | $2.4 \times 10^3 \pm 1.2 \times 10^3$ | $6.5 \times 10^{-5} \pm 2.1 \times 10^{-5}$ | $2.7 \times 10^{-8}$ |
|  | BMP-4 (86%) | $4.2 \times 10^3 \pm 0.2 \times 10^3$ | $5.1 \times 10^{-4} \pm 0.1 \times 10^{-4}$ | $1.2 \times 10^{-7}$ |
|  | BMP-6 (57%) | $2.9 \times 10^3 \pm 0.5 \times 10^3$ | $2.1 \times 10^{-3} \pm 0.3 \times 10^{-3}$ | $7.1 \times 10^{-7}$ |
| h-Fetuin | BMP-2 | $2.2 \times 10^4 \pm 0.5 \times 10^4$ | $1.1 \times 10^{-3} \pm 0.1 \times 10^{-3}$ | $5.1 \times 10^{-8}$ |
| TRH1 (b-fetuin) | BMP-2 | $1.3 \times 10^3 \pm 0.5 \times 10^3$ | $3.8 \times 10^{-3} \pm 0.5 \times 10^{-3}$ | $2.4 \times 10^{-6}$ |
|  | TGF-β1 | — | — | $>10^{-5}$ |
| (reduced) | BMP-2 | — | — | $>10^{-5}$ |
| loop2 (b-fetuin) | BMP-2 | — | — | $>10^{-5}$ |
| TRH1 (TβRII) | BMP-2 | — | — | $>10^{-5}$ |
|  | TGF-β1 | $2.2 \times 10^3 \pm 1.3 \times 10^3$ | $2.3 \times 10^{-3} \pm 0.5 \times 10^{-3}$ | $1.0 \times 10^{-6}$ |
| (reduced) | TGF-β1 | — | — | $>10^{-5}$ |

Binding constants for fetuins and TRH1 peptide interactions with TGF-β and BMPs measured using the BIAcore and BIA-evaluation software (Pharmacia Biosensor). The change in response with time was plotted for each analyte concentration (ie. dR/dT vs R), and the slope of these lines were then plotted as a function of analyte concentration (i.e d(dR/dT)/dR vs C), where the slope yields $k_{ass}$. The dissociation rate constant, $k_{diss}$, is obtained after analyte injection is discontinued as the slope of $\ln(R_{tl}/R_{tn})$ vs time. $K_D$s are $k_{diss}/k_{ass}$. Variance for $k_{ass}$ is standard error of the linear regression plot, and for $k_{diss}$ values are the mean ± range of 3 or more independent injections. Steady-state was observed for fetuin - TGF-β1 binding, and analysis of these data by Scatchard plots produced a similar $K_D$ value, $4.6 \times 10^{-6}$M. Bracketed numbers are percent homology of the cytokines relative to BMP-2. Methods, TGF-βs and BMPs were immobilized onto the carboxy-methylated dextran surface of the CM5 sensor chip. 1000 R.U. equals approximately 1 ng/mm$^2$. The running buffer was 20 mM Hepes (pH 7.2), 150 mM NaCl and the flow rate was 3 ul/min. Bovine fetal fetuin (Sigma, Mo) and adult human fetuin/α2-HS glycoprotein (Calbiochem, Ca) were purified by the manufacturers using different protocols. Regeneration of the surface to remove bound analyte was done by injecting of 10 ul of 20 mM NaOH. To cycilize TRH1 peptides, the material was reduced with 5 mM DTT then brought to a final concentration of 60 uM in 25 mM ammonium acetate (pH 8.5). After stirring in the dark for 30 min at 20° C. with 30 mM potassium ferricyanide, the peptide was mixed with AG3-X4A resin (BioRad), filtered, lyophilization and desalted on a 50 × 2.5 cm column of Biogel P2 (Pharmacia) developed in water, and further purified by reverse phase HPLC. Ion spray mass spectroscopy confirmed cyclization and lack of peptide cross-linking.

We claim:

1. A composition consisting of at least one TGFβ receptor II homology 1b (TRH1b) subdomain and a carrier, auxiliary or excipient, wherein the TRH1b subdomain has a sequence with the following amino acid pattern: Cys—$X_j$—Lys/Arg—$X_k$—Ser/Thr—$X_l$—Cys—$X_m$—Asp—$X_n$—Asp/Glu, wherein $X_j$, $X_k$, $X_l$, $X_m$, $X_n$, represent any amino acid and j is 4 to 5, k is 2 to 6, l is 4 to 9, m is 0 to 2, and n is 5 to 6.

2. A composition consisting of at least one TGFβ receptor II homology 1 (TRH1) domain, and a carrier, auxiliary or excipient, wherein the TRH1 domain has a sequence with the following amino acid pattern: Cys—$X_h$—Asn/Gln—$X_i$—Cys—$X_j$—Lys/Arg—$X_k$—Ser/Thr—$X_l$—Cys—$X_m$—ASP—$X_n$—Asp/Glu, wherein $X_h$, $X_i$, $X_j$, $X_k$, $X_l$, $X_m$, $X_n$, represent any amino acid and h is 8 to 14, i is 12 to 16, j is 4 to 5, k is 2 to 6, l is 4 to 9, m is 0 to 2, and n is 5 to 6.

3. A composition as claimed in claim 2 wherein the TRH1 domain is the TRH1 domain of TGFβ type I receptor having the amino acid sequence shown in SEQ. ID. NO. 8.

4. A chimeric protein having the amino acid sequence of fetuin with the TGFβ receptor homology domain 1b region shown in SEQ. ID. NO. 5 replaced with a TGFβ receptor homology domain 1b region of TGFβ type II receptor shown in SEQ. ID. NO. 6, or replaced with a TGFβ receptor homology domain 1b region of thyroglobulin as shown in SEQ ID NO. 7.

5. A composition as claimed in claim 4 wherein the fetuin has one of the amino acid sequences shown in SEQ. ID. NO. 10, 11, 12, 13, or 14.

6. A chimeric protein having the amino acid sequence of fetuin with the TGFβ receptor homology domain 1 region shown in SEQ. ID. NO. 2 replaced with a TGFβ receptor homology domain 1 region of TGFβ type II receptor shown in SEQ. ID. NO. 3, or replaced with a TGFβ receptor homology domain 1b region of thyroglobulin as shown in SEQ. ID. NO. 4.

7. A composition as claimed in claim 6 wherein the fetuin has an amino acid sequence as shown in any one of SEQ. ID. NO. 10, 11, 12, 13, or 14.

* * * * *

SEQUENCE LISTING

<160> NUMBER OF SEQ ID NOS: 14

<210> SEQ ID NO 1
<211> LENGTH: 567
<212> TYPE: PRT
<213> ORGANISM: Homo sapiens

<400> SEQUENCE: 1

```
Met Gly Arg Gly Leu Leu Arg Gly Leu Trp Pro Leu His Ile Val Leu
 1               5                  10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
    290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365
```

```
Gly Arg Pro Lys Met Pro Ile Val His Arg Asp Leu Lys Ser Ser Asn
370                 375                 380
Ile Leu Val Lys Asn Asp Leu Thr Cys Leu Cys Asp Phe Gly Leu
385                 390                 395                 400
Ser Leu Arg Leu Asp Pro Thr Leu Ser Val Asp Asp Leu Ala Asn Ser
            405                 410                 415
Gly Gln Val Gly Thr Ala Arg Tyr Met Ala Pro Glu Val Leu Glu Ser
            420                 425                 430
Arg Met Asn Leu Glu Asn Ala Glu Ser Phe Lys Gln Thr Asp Val Tyr
        435                 440                 445
Ser Met Ala Leu Val Leu Trp Glu Met Thr Ser Arg Cys Asn Ala Val
450                 455                 460
Gly Glu Val Lys Asp Tyr Glu Pro Pro Phe Gly Ser Lys Val Arg Glu
465                 470                 475                 480
His Pro Cys Val Glu Ser Met Lys Asp Asn Val Leu Arg Asp Arg Gly
                485                 490                 495
Arg Pro Glu Ile Pro Ser Phe Trp Leu Asn His Gln Gly Ile Gln Met
                500                 505                 510
Val Cys Glu Thr Leu Thr Glu Cys Trp Asp His Asp Pro Glu Ala Arg
            515                 520                 525
Leu Thr Ala Gln Cys Val Ala Glu Arg Phe Ser Glu Leu Glu His Leu
            530                 535                 540
Asp Arg Leu Ser Gly Arg Ser Cys Ser Glu Glu Lys Ile Pro Glu Asp
545                 550                 555                 560
Gly Ser Leu Asn Thr Thr Lys
                565

<210> SEQ ID NO 2
<211> LENGTH: 45
<212> TYPE: PRT
<213> ORGANISM: Homo sapiens

<400> SEQUENCE: 2

Cys His Val Leu Asp Pro Thr Pro Leu Ala Asn Cys Ser Val Arg Gln
1               5                   10                  15
Gln Thr Gln His Ala Val Glu Gly Asp Cys Asp Ile His Val Leu Lys
            20                  25                  30
Gln Asp Gly Gln Phe Ser Val Leu Phe Thr Lys Cys Asp
        35                  40                  45

<210> SEQ ID NO 3
<211> LENGTH: 43
<212> TYPE: PRT
<213> ORGANISM: Homo sapiens

<400> SEQUENCE: 3

Cys Asp Asn Gln Lys Ser Cys Met Ser Asn Cys Ser Ile Thr Ser Ile
1               5                   10                  15
Cys Glu Lys Pro Gln Glu Val Cys Val Ala Val Trp Arg Lys Asn Asp
            20                  25                  30
Glu Asn Ile Thr Leu Glu Thr Val Cys His Asp
        35                  40

<210> SEQ ID NO 4
<211> LENGTH: 44
<212> TYPE: PRT
<213> ORGANISM: Homo sapiens
```

-continued

```
<400> SEQUENCE: 4

Cys Ser Ala Asp Tyr Ser Gly Leu Leu Leu Ala Phe Gln Val Phe Leu
  1               5                  10                  15

Leu Asp Glu Leu Thr Ala Arg Gly Phe Cys Gln Ile Val Lys Thr
             20                  25                  30

Ala Gly Thr Pro Val Ser Ile Pro Val Cys Asp Asp
             35                  40

<210> SEQ ID NO 5
<211> LENGTH: 20
<212> TYPE: PRT
<213> ORGANISM: Homo sapiens

<400> SEQUENCE: 5

Cys Asp Ile His Val Leu Lys Gln Asp Gly Gln Phe Ser Val Leu Phe
  1               5                  10                  15

Thr Lys Cys Asp
             20

<210> SEQ ID NO 6
<211> LENGTH: 20
<212> TYPE: PRT
<213> ORGANISM: Homo sapiens

<400> SEQUENCE: 6

Cys Val Ala Val Trp Arg Lys Asn Asp Glu Asn Ile Thr Leu Glu Thr
  1               5                  10                  15

Val Cys His Asp
             20

<210> SEQ ID NO 7
<211> LENGTH: 19
<212> TYPE: PRT
<213> ORGANISM: Homo sapiens

<400> SEQUENCE: 7

Cys Gln Ile Gln Val Lys Thr Ala Gly Thr Pro Val Ser Ile Pro Val
  1               5                  10                  15

Cys Asp Asp

<210> SEQ ID NO 8
<211> LENGTH: 26
<212> TYPE: PRT
<213> ORGANISM: Unknown
<220> FEATURE:
<223> OTHER INFORMATION: Description of Unknown Organism:mTGF-BRI

<400> SEQUENCE: 8

Cys Gly Asn Glu Asp His Cys Glu Gly Gln Cys Phe Ser Ser Leu Ser
  1               5                  10                  15

Ile Tyr Asp Gly Phe His Val Tyr Gln Lys
             20                  25

<210> SEQ ID NO 9
<211> LENGTH: 34
<212> TYPE: PRT
<213> ORGANISM: Unknown
<220> FEATURE:
<223> OTHER INFORMATION: Description of Unknown Organism:hTGFBRII

<400> SEQUENCE: 9

Cys Asp Asn Gln Lys Ser Cys Met Ser Asn Cys Ser Ile Thr Ser Ile
  1               5                  10                  15
```

```
Cys Glu Lys Pro Gln Glu Val Cys Val Ala Val Trp Arg Lys Asn Asp
             20                  25                  30

Glu Asn

<210> SEQ ID NO 10
<211> LENGTH: 364
<212> TYPE: PRT
<213> ORGANISM: Unknown
<220> FEATURE:
<223> OTHER INFORMATION: Description of Unknown Organism:Sheep

<400> SEQUENCE: 10

Met Lys Ser Phe Leu Leu Phe Cys Leu Ala Gln Leu Cys Ser Cys
 1               5                  10                  15

Arg Ser Ile Pro Leu Asp Pro Ile Ala Gly Tyr Lys Glu Pro Ala Cys
             20                  25                  30

Asp Asp Pro Asp Thr Glu Gln Ala Ala Leu Ala Ala Val Asp Tyr Ile
         35                  40                  45

Asn Lys His Leu Pro Arg Gly Tyr Lys His Thr Leu Asn Gln Ile Asp
     50                  55                  60

Ser Val Lys Val Trp Pro Arg Arg Pro Thr Gly Glu Val Tyr Asp Ile
 65                  70                  75                  80

Glu Ile Asp Thr Leu Glu Thr Thr Cys His Val Leu Asp Pro Thr Pro
                 85                  90                  95

Leu Val Asn Cys Ser Val Arg Gln Gln Thr Glu His Ala Val Glu Gly
            100                 105                 110

Asp Cys Asp Ile His Val Leu Lys Gln Asp Gly Gln Phe Ser Val Leu
        115                 120                 125

Phe Thr Lys Cys Asp Ser Ser Pro Asp Ser Ala Glu Asp Val Arg Lys
    130                 135                 140

Leu Cys Pro Asp Cys Pro Leu Leu Ala Pro Leu Asn Asn Ser Gln Val
145                 150                 155                 160

Val His Ala Ala Glu Val Ala Leu Ala Thr Phe Asn Ala Gln Asn Asn
                165                 170                 175

Gly Ser Tyr Phe Gln Leu Val Glu Ile Ser Arg Ala Gln Phe Val Pro
            180                 185                 190

Leu Pro Gly Ser Val Ser Val Glu Phe Ala Val Ala Ala Thr Asp Cys
        195                 200                 205

Ile Ala Lys Glu Val Val Asp Pro Thr Lys Cys Asn Leu Leu Ala Glu
    210                 215                 220

Lys Gln Tyr Gly Phe Cys Lys Gly Ser Val Ile Gln Lys Ala Leu Gly
225                 230                 235                 240

Gly Glu Asp Val Thr Val Thr Cys Thr Leu Phe Gln Thr Gln Pro Val
                245                 250                 255

Ile Pro Gln Pro Gln Pro Glu Gly Ala Glu Ala Gly Ala Pro Ser Ala
            260                 265                 270

Val Pro Asp Ala Ala Val Pro Asp Ala Val Pro Ala Pro Ser Ala
        275                 280                 285

Ala Gly Leu Pro Val Gly Ser Val Ala Gly Pro Ser Val Val Ala
    290                 295                 300

Val Pro Leu Pro Leu His Arg Ala His Tyr Asp Leu Arg His Thr Phe
305                 310                 315                 320

Ser Gly Val Ala Ser Val Glu Ser Ala Ser Gly Glu Ala Phe His Val
                325                 330                 335

Gly Lys Thr Pro Ile Val Gly Gln Pro Ser Val Pro Gly Gly Pro Val
```

```
                    340              345              350
His Leu Cys Pro Gly Arg Ile Arg Tyr Phe Lys Ile
            355              360
```

<210> SEQ ID NO 11
<211> LENGTH: 359
<212> TYPE: PRT
<213> ORGANISM: Unknown
<220> FEATURE:
<223> OTHER INFORMATION: Description of Unknown Organism:Bovine

<400> SEQUENCE: 11

```
Met Lys Ser Phe Val Leu Leu Phe Cys Leu Ala Gln Leu Trp Gly Cys
 1               5                  10                  15

His Ser Ile Pro Leu Asp Pro Val Ala Gly Tyr Lys Glu Pro Ala Cys
            20                  25                  30

Asp Asp Pro Asp Thr Glu Gln Ala Ala Leu Ala Ala Val Asp Tyr Ile
        35                  40                  45

Asn Lys His Leu Pro Arg Gly Tyr Lys His Thr Leu Asn Gln Ile Asp
    50                  55                  60

Ser Val Lys Val Trp Pro Arg Arg Pro Thr Gly Glu Val Tyr Asp Ile
65                  70                  75                  80

Glu Ile Asp Thr Leu Glu Thr Thr Cys His Val Leu Asp Pro Thr Pro
                85                  90                  95

Leu Ala Asn Cys Ser Val Arg Gln Gln Thr Gln His Ala Val Glu Gly
            100                 105                 110

Asp Cys Asp Ile His Val Leu Lys Gln Asp Gly Gln Phe Ser Val Leu
        115                 120                 125

Phe Thr Lys Cys Asp Ser Ser Pro Asp Ser Ala Glu Asp Val Arg Lys
    130                 135                 140

Leu Cys Pro Asp Cys Pro Leu Leu Ala Pro Leu Asn Asp Ser Arg Val
145                 150                 155                 160

Val His Ala Val Glu Val Ala Leu Ala Thr Phe Asn Ala Glu Ser Asn
                165                 170                 175

Gly Ser Tyr Leu Gln Leu Val Glu Ile Ser Arg Ala Gln Phe Val Pro
            180                 185                 190

Leu Pro Val Ser Val Ser Val Glu Phe Ala Val Ala Ala Thr Asp Cys
        195                 200                 205

Ile Ala Lys Glu Val Val Asp Pro Thr Lys Cys Asn Leu Leu Ala Glu
    210                 215                 220

Lys Gln Tyr Gly Phe Cys Lys Gly Ser Val Ile Gln Lys Ala Leu Gly
225                 230                 235                 240

Gly Glu Asp Val Arg Val Thr Cys Thr Leu Phe Gln Thr Gln Pro Val
                245                 250                 255

Ile Pro Gln Pro Gln Pro Asp Gly Ala Glu Ala Glu Ala Pro Ser Ala
            260                 265                 270

Val Pro Asp Ala Ala Gly Pro Thr Pro Ser Ala Gly Pro Pro Val
        275                 280                 285

Ala Ser Val Val Gly Pro Ser Val Ala Val Pro Leu Pro Leu
    290                 295                 300

His Arg Ala His Tyr Asp Leu Arg His Thr Phe Ser Gly Val Ala Ser
305                 310                 315                 320

Val Glu Ser Ser Ser Gly Glu Ala Phe His Val Gly Lys Thr Pro Ile
                325                 330                 335

Val Gly Gln Pro Ser Ile Pro Gly Gly Pro Val Arg Leu Cys Pro Gly
```

340                 345                 350

Arg Ile Arg Tyr Phe Lys Ile
        355

<210> SEQ ID NO 12
<211> LENGTH: 352
<212> TYPE: PRT
<213> ORGANISM: Unknown
<220> FEATURE:
<223> OTHER INFORMATION: Description of Unknown Organism:Rat

<400> SEQUENCE: 12

Met Lys Ser Leu Val Leu Leu Cys Phe Ala Gln Leu Trp Ser Cys
 1               5                  10                  15

Gln Ser Ala Pro Gln Gly Ala Gly Leu Gly Phe Arg Glu Leu Ala Cys
             20                  25                  30

Asp Asp Pro Glu Thr Glu His Val Ala Leu Ile Ala Val Asp Tyr Leu
             35                  40                  45

Asn Lys His Leu Leu Gln Gly Phe Arg Gln Ile Leu Asn Gln Ile Asp
         50                  55                  60

Lys Val Lys Val Trp Ser Arg Arg Pro Phe Gly Val Tyr Glu Leu
 65                  70                  75                  80

Glu Ile Asp Thr Leu Glu Thr Thr Cys His Ala Leu Asp Pro Thr Pro
                     85                  90                  95

Leu Ala Asn Cys Ser Val Arg Gln Gln Ala Glu His Ala Val Glu Gly
                100                 105                 110

Asp Cys Asp Phe His Ile Leu Lys Gln Asp Gly Gln Phe Arg Val Leu
            115                 120                 125

His Ala Gln Cys His Ser Thr Pro Asp Ser Ala Glu Asp Val Arg Lys
        130                 135                 140

Phe Cys Pro Arg Cys Pro Ile Leu Ile Arg Phe Asn Asp Thr Asn Val
145                 150                 155                 160

Val His Thr Val Lys Thr Ala Leu Ala Ala Phe Asn Ala Gln Asn Asn
                    165                 170                 175

Gly Thr Tyr Phe Lys Leu Val Glu Ile Ser Arg Ala Gln Asn Val Pro
                180                 185                 190

Phe Pro Val Ser Thr Leu Val Glu Phe Val Ile Ala Thr Asp Cys
            195                 200                 205

Thr Gly Gln Glu Val Thr Asp Pro Ala Lys Cys Asn Leu Leu Ala Glu
        210                 215                 220

Lys Gln Tyr Gly Phe Cys Lys Ala Thr Leu Ile His Arg Leu Gly Gly
225                 230                 235                 240

Glu Glu Val Ser Val Ala Cys Lys Leu Phe Gln Thr Gln Pro Gln Pro
                    245                 250                 255

Ala Asn Ala Asn Pro Ala Gly Pro Ala Pro Thr Val Gly Gln Ala Ala
                260                 265                 270

Pro Val Ala Pro Pro Ala Gly Pro Pro Glu Ser Val Val Gly Pro
            275                 280                 285

Val Ala Val Pro Leu Gly Leu Pro Asp His Arg Thr His His Asp Leu
        290                 295                 300

Arg His Ala Phe Ser Pro Val Ala Ser Val Glu Ser Ala Ser Gly Glu
305                 310                 315                 320

Val Leu His Ser Pro Lys Val Gly Gln Pro Gly Asp Ala Gly Ala Ala
                    325                 330                 335

Gly Pro Val Ala Pro Leu Cys Pro Gly Arg Val Arg Tyr Phe Lys Ile 340        345        350

<210> SEQ ID NO 13
<211> LENGTH: 362
<212> TYPE: PRT
<213> ORGANISM: Unknown
<220> FEATURE:
<223> OTHER INFORMATION: Description of Unknown Organism:Pig

<400> SEQUENCE: 13

Ile Leu Phe Phe Cys Leu Ala Gln Leu Trp Gly Cys Arg Ala Val Pro
 1               5                  10                  15

His Gly Pro Ile Leu Gly Tyr Arg Glu Pro Ala Cys Asp Asp Val Glu
                20                  25                  30

Thr Glu Gln Ala Ala Leu Ala Val Asp Tyr Ile Asn Lys His Leu
            35                  40                  45

Pro Arg Gly Tyr Lys His Thr Leu Asn Gln Val Asp Ser Val Lys Val
    50                  55                  60

Trp Pro Arg Arg Pro Ala Gly Glu Val Phe Asp Ile Glu Ile Asp Thr
65                  70                  75                  80

Leu Glu Thr Thr Cys His Val Leu Asp Pro Thr Pro Leu Ala Asn Cys
                85                  90                  95

Ser Val Arg Gln Gln Leu Thr Glu His Ala Val Glu Gly Asp Cys Asp
                100                 105                 110

Phe His Val Leu Lys Gln Asp Gly Gln Phe Ser Val Leu Phe Ala Lys
            115                 120                 125

Cys Asp Ser Ser Pro Asp Ser Ala Glu Asp Val His Lys Val Cys Pro
        130                 135                 140

Asn Cys Pro Leu Leu Ala Pro Leu Asn Asp Ser Arg Val Val His Ala
145                 150                 155                 160

Ala Glu Ser Ala Leu Ala Ala Phe Asn Ala Gln Ser Asn Gly Ser Tyr
                165                 170                 175

Leu Gln Leu Val Glu Ile Ser Arg Ala Gln Leu Val Pro Leu Ser Ala
            180                 185                 190

Ser Val Ser Val Glu Phe Ala Val Ala Val Thr Asp Cys Val Ala Lys
        195                 200                 205

Glu Ala Tyr Ser Pro Thr Lys Cys Asn Leu Leu Val Glu Lys Gln Tyr
    210                 215                 220

Gly Phe Cys Lys Gly Thr Val Thr Ala Lys Val Asn Glu Glu Asp Val
225                 230                 235                 240

Ala Val Thr Cys Thr Val Phe Gln Thr Gln Pro Val Leu Val Gln Pro
                245                 250                 255

Gln Pro Ala Gly Ala Asp Ala Gly Ala Thr Pro Val Val Asp Ala Ala
            260                 265                 270

Ala Thr Ala Ser Pro Leu Ala Asp Val Pro Ala Ala Ser Leu Val Val
        275                 280                 285

Gly Pro Met Val Val Ala Val Pro Pro Gly Ile Pro Pro Val His Arg
    290                 295                 300

Ser His Tyr Asp Leu Arg His Ser Phe Ser Gly Val Ala Ser Val Glu
305                 310                 315                 320

Ser Ala Ser Gly Glu Ala Phe His Val Gly Lys Thr Pro Lys Gly Ala
                325                 330                 335

Gln Pro Ser Ile Pro Ala Ala Asp Gly Ser Val Pro Val Val Arg Pro
            340                 345                 350

Cys Pro Gly Arg Ile Arg His Phe Lys Ile

<210> SEQ ID NO 14
<211> LENGTH: 367
<212> TYPE: PRT
<213> ORGANISM: Homo sapiens

<400> SEQUENCE: 14

```
Met Lys Ser Leu Val Leu Leu Cys Leu Ala Gln Leu Trp Gly Cys
  1               5                  10                  15

His Ser Ala Pro His Gly Pro Gly Leu Ile Tyr Arg Gln Pro Asn Cys
             20                  25                  30

Asp Asp Pro Glu Thr Glu Glu Ala Ala Leu Val Ala Ile Asp Tyr Ile
         35                  40                  45

Asn Gln Asn Leu Pro Trp Gly Tyr Lys His Thr Leu Asn Gln Ile Asp
     50                  55                  60

Glu Val Lys Val Trp Pro Gln Gln Pro Ser Gly Glu Leu Phe Glu Ile
 65                  70                  75                  80

Glu Ile Asp Thr Leu Glu Thr Thr Cys His Val Leu Asp Pro Thr Pro
                 85                  90                  95

Val Ala Arg Cys Ser Val Arg Gln Leu Lys Glu His Ala Val Glu Gly
            100                 105                 110

Asp Cys Asp Phe Gln Leu Leu Lys Leu Asp Gly Lys Phe Ser Val Val
        115                 120                 125

Tyr Ala Lys Cys Asp Ser Ser Pro Asp Ser Ala Glu Asp Val Arg Lys
    130                 135                 140

Val Cys Gln Asp Cys Pro Leu Leu Ala Pro Leu Asn Asp Thr Arg Val
145                 150                 155                 160

Val His Ala Ala Lys Ala Ala Leu Ala Ala Phe Asn Ala Gln Asn Asn
                165                 170                 175

Gly Ser Asn Phe Gln Leu Glu Glu Ile Ser Arg Ala Gln Leu Val Pro
            180                 185                 190

Leu Pro Pro Ser Thr Tyr Val Gly Phe Thr Val Ser Gly Thr Asp Cys
        195                 200                 205

Val Ala Lys Glu Ala Thr Glu Ala Ala Lys Cys Asn Leu Leu Ala Glu
    210                 215                 220

Lys Gln Tyr Gly Phe Cys Lys Ala Thr Leu Ser Glu Lys Leu Gly Gly
225                 230                 235                 240

Ala Glu Val Ala Val Thr Cys Thr Val Phe Gln Thr Gln Pro Val Thr
                245                 250                 255

Ser Gln Pro Gln Pro Glu Gly Ala Asn Glu Ala Val Pro Thr Pro Val
            260                 265                 270

Val Asp Pro Asp Ala Pro Pro Ser Pro Pro Leu Gly Ala Pro Gly Leu
        275                 280                 285

Pro Pro Ala Gly Ser Pro Pro Asp Ser His Val Leu Leu Ala Ala Pro
    290                 295                 300

Pro Gly His Gln Leu His Arg Ala His Tyr Asp Leu Arg His Thr Phe
305                 310                 315                 320

Met Gly Val Val Ser Leu Gly Ser Pro Ser Gly Glu Val Ser His Pro
                325                 330                 335

Arg Lys Thr Arg Thr Val Val Gln Pro Ser Val Gly Ala Ala Ala Gly
            340                 345                 350

Pro Val Val Pro Pro Cys Pro Gly Arg Ile Arg His Phe Lys Val
        355                 360                 365
```